US012370153B2

(12) United States Patent
Dusci

(10) Patent No.: US 12,370,153 B2
(45) Date of Patent: Jul. 29, 2025

(54) READY-TO-USE KETAMINE PREMIX FORMULATION

(71) Applicant: INFORLIFE SA, Campascio (CH)

(72) Inventor: Sergio Dusci, Tresivio (IT)

(73) Assignee: INFORLIFE SA, Campascio (CH)

(*) Notice: Subject to any disclaimer, the term of this patent is extended or adjusted under 35 U.S.C. 154(b) by 0 days.

(21) Appl. No.: 18/770,514

(22) Filed: Jul. 11, 2024

(65) Prior Publication Data
US 2025/0025431 A1    Jan. 23, 2025

Related U.S. Application Data

(60) Provisional application No. 63/513,225, filed on Jul. 12, 2023.

(51) Int. Cl.
| | | |
|---|---|---|
| A61K 31/135 | (2006.01) | |
| A61K 45/06 | (2006.01) | |
| A61M 5/14 | (2006.01) | |

(52) U.S. Cl.
CPC ........... *A61K 31/135* (2013.01); *A61K 45/06* (2013.01); *A61M 5/14* (2013.01); *A61M 2005/1401* (2013.01)

(58) Field of Classification Search
CPC .................................................. A61K 31/135
See application file for complete search history.

(56) References Cited

U.S. PATENT DOCUMENTS

| | | | |
|---|---|---|---|
| 5,439,643 A | 8/1995 | Liebert | |
| 8,617,467 B2 | 12/2013 | Rodriguez et al. | |
| 11,207,309 B2 * | 12/2021 | Conrad | A61K 31/4468 |

OTHER PUBLICATIONS

Ketalar (ketamine hydrochloride) injection, for intravenous or intramuscular use, CIII, NDA016812, revised Jun. 2022.*
Ketamine Hydrochloride-ketamine hydrochloride injection, solution, concentrate, Hospira-ANDA 074549, 2022 (23 pages).
Ketamine Hydrochloride-ketamine hydrochloride injection, Hikma-ANDA 074524, 2022 (20 pages).
Ketamine Hydrochloride-ketamine hydrochloride injection, AuroMedics-ANDA 076092, 2022 (28 pages).
Ketalar (ketamine hydrochloride) injection, for intravenous or intramuscular use, CIII, NDA016812, 2022 (13 pages).
<785> Osmolality and Osmolarity, (http://www.uspbpep.com/usp31/v31261/usp31nf26s1_c785.asp), Pharmacopeial Forum : vol. No. 34(1), 2024 (3 pages).
<1222> Terminally Sterilized Pharmaceutical Products—Parametric Release, (https://www.uspnf.com/purchase-usp-nf#:~:text=The%20current%20version%20of%20USP,official%20on%20May%201%2C%202024), United States Pharmacopeia (2024). (7 pages).
Department of Health and Human Services, FDA-2022-D-0219, Human Prescription Drug and Biological Products-Labeling for Dosing Based on Weight or Body Surface Area for Ready-to-Use Containers—"Dose Banding", Guidance for Industry, pp. 2-3 (2023); (10 pages).
"An Overview of Compounding", in 2; National Academies of Sciences, Engineering, and Medicine; Health and Medicine Division; Board on Health Sciences Policy; Committee on the Clinical Utility of Treating Patients with Compounded Bioidentical Hormone Replacement Therapy: A Review of Safety, Effectiveness, and Use.; National Academies Press; Jul. 1, 2020; (10 pages).
"Parenteral Preparations: Formulation Challenges"; Manufacturing Chemist, Feb. 6, 2017; https://www.manufacturingchemist.com/news/article_page/Parenteral_preparations_formulation_challenges/125615; (8 pages).
N.P. Shah, et al.; "Do You Know the Difference Between Extractables and Leachables?"; Azenta Life Sciences; Jul. 10, 2019; https://www.azenta.com/blog/do-you-know-difference-between-extractables-and-leachables; (6 pages).
T. Ofenböck; "Terminal Sterilisation of Parenteral Drugs"; Process Tech. Online; Feb. 18, 2022; https://process-technology-online.com/pharma/terminal-sterilisation-of-parenteral-drugs/; (5 pages).
Carlos L. Errando et al.; "Letters to the Editor"; Regional Anesthesia and Pain Medicine; 23(3); 323-329; 1998 (1 page).
Lyvia Maria R. S. Gomes et al.; "Neurotoxicity of Subarachnoid Preservative-Free S (+)-Ketamine in Dogs"; Pain Physician 2011; 14:83-90 (8 pages).
Beatriz Merchel Piovesan Pereira et al.; "Benzalkonium Chlorides: Uses, Regulatory Status, and Microbial Resistance"; Applied and Environmental Microbiology; Jul. 2019; vol. 85; Issue 13 (13 pages).
U.S. Department of Health and Human Services, FDA-2022-D-0219, Temporary Policies for Compounding Certain Parenteral Drug Products; Guidance for Industry, p. 12 (2024) (18 pages).
Jean-Marc Malinovsky et al.; "Is Ketamine or It's Preservative Responsible for Neurotoxicity in the Rabbit?"; Anesthesiology; 78:109-115; 1993 (7 pages).
Huddy et al.; "Preservative-free ketamine"; British journal of anaesthesia, 92(1), 152; 2004 (1 page).
Martin Stotz et al.; "Histological Findings After Long-Term Infusion of Intrathecal Ketamine for Chronic Pain: A Case Report"; Journal of Pain and Symptom Management; vol. 18 No. 3; Sep. 1999; (6 pages).
D. A. H. de Beer et al.; "Caudal additives in children-solutions or problems?"; British Journal of Anaesthesia; 90 (4): 487-98; 2003 (12 pages).

(Continued)

*Primary Examiner* — Svetlana M Ivanova
(74) *Attorney, Agent, or Firm* — Rothwell, Figg, Ernst & Manbeck, P.C.

(57) ABSTRACT

The invention relates to a sterile, ready-to-use, stable aqueous solution of ketamine suitable for direct intravenous infusion to a patient in need thereof, wherein the composition is disposed within a sealed infusion container as a premixture. The invention further relates to aqueous solutions of ketamine that are free of antimicrobials such as benzethonium chloride and are shelf-stable. The pharmaceutical compositions can be used, for example, wherein the subject is in need of anesthesia for a diagnostic or a surgical procedure.

23 Claims, 8 Drawing Sheets

(56) References Cited

OTHER PUBLICATIONS

U.S. Department of Health and Human Services, FDA-2014-D-0779, Current Good Manufacturing Practice-Guidance for Human Drug Compounding Outsourcing Facilities Under Section 503B of the FD&C Act, p. 44 (2020) (51 pages).
"<797> Pharmaceutical Compounding-Sterile Preparations"; The United States Pharmacopeial Convention; 2008 (61 pages).

* cited by examiner

READY-TO-USE KETAMINE PREMIX FORMULATION

CROSS-REFERENCE TO RELATED APPLICATIONS

This application claims priority benefit of U.S. provisional application No. 63/513,225, filed Jul. 12, 2023 the disclosure of which is incorporated herein by reference in its entirety.

TECHNICAL FIELD

The present invention relates to ready-to-use, sterile, premixed formulations of ketamine, or a pharmaceutically acceptable salt thereof, that does not include benzethonium chloride, is chemically stable for approximately 24 months or more, and can be used, for example, to treat a subject in need of anesthesia for a diagnostic or a surgical procedure.

BACKGROUND

Ketamine hydrochloride is a nonbarbiturate anesthetic chemically designated (RS)-2-(2-chlorophenyl)-2-(methylamino)cyclohexanone hydrochloride. Ketamine is a noncompetitive, high affinity NMDA receptor antagonist. Ketamine's mechanism of action is primarily due to antagonism of N-methyl-D-aspartate (NMDA receptors) in the central nervous system. Ketamine has been used as an anesthetic agent.

Most preparations of ketamine contain equal (1:1) concentrations of its two enantiomers: S (+) ketamine and R (−) ketamine. Ketamine formulations that are commercially available and approved by the FDA in the U.S. currently contain benzethonium chloride added as a preservative.

Ketamine can be administered to a patient in a variety of ways. For example, ketamine can be used as the sole anesthetic agent for diagnostic and surgical procedures that do not require skeletal muscle relaxation. Alternatively, ketamine can be administered for the induction of anesthesia prior to the administration of other general anesthetic agents or as a supplement to other anesthetic agents.

The container closure system of a product intended for parenteral use has to ensure continuous compliance with the storage and handling specifications throughout the product shelf life to maintain functionality and drug delivery accuracy. Several factors have to be considered when choosing the right container closure system for an injectable product, such as drug product formulation properties, dosage, type of application, stability, stability when subjected to extreme conditions (such as during terminal sterilization), sterility, container closure integrity, storage conditions and duration, and end-user friendliness. Thus, there is a need to develop container closure systems that are appropriate for specific injectable products that maintains functionality and drug delivery accuracy.

Vials are the most common primary packaging for administration of ketamine injectables on the market in the U.S. Such vials contain concentrated ketamine solution. For intravenous (IV) administration, it is necessary to introduce the ketamine solution into an infusion container containing a suitably diluted IV solution. Thus, to date, ketamine has been provided as a concentrate that must be diluted with sterile water for injection (WFI), a sodium chloride solution, saline, or a dextrose in water solution prior to administration to a patient and must be used immediately after dilution. If the entire vial is not required, then the vial must still be disposed of as the vials are single use only.

There is no available single intravenous dosage form that provides a sterile, ready-to-use, stable, liquid formulation of ketamine that can be administered without any manipulation to a patient in need thereof, thereby avoiding a compromise with the sterility, an error in dosing accuracy and/or in medicament preparation etc. There is a need for a sterile, ready to use infusion container comprising a shelf-stable, liquid formulation of ketamine which can be administered to a patient in need thereof without deviation or manipulations and while preserving the sterility of the product, and optionally with a provision for administering along with other medicaments for combination or sequential therapy, if needed or desired. There also is a need for a sterile, ready to use infusion container comprising a shelf-stable, liquid formulation of ketamine that does not contain a preservative or antimicrobial such as benzethonium chloride. Preferably the shelf-life of the sterile, ready to use ketamine solution will be 24 months or more at room temperature.

SUMMARY OF THE INVENTION

In the present invention, the inventors have overcome multiple problems of prior art ketamine formulations, such as additional costs and inconvenience; the risk of potential contamination due to inadvertent medical error; long-term storage of a ready to use dosage of a stable, preservative-free ketamine solution. The inventors have developed a sterile, stable liquid formulation of ketamine in an infusion container that is at a ready to use concentration. For plastic materials being considered for use as primary packing materials for the infusion container, the challenge has been to develop packaging that is compatible with the contents, minimizes extractables/leachables, are solvent-resistant, and are durable. The packaging of a pharmaceutical product should desirably be stable and mutually compatible under terminal sterilization conditions, as packaging materials and terminal sterilization can affect the condition of different formulations. A sterile ready to use ketamine formulation in an infusion container avoids the expense, inconvenience, delay, and risk of contamination, and provides significant advantages over currently available concentrated formulations. Additionally, the inventors have beneficially developed a formulation of ketamine that is shelf-stable in an infusion container for greater than three months, and preferably for 24 months or more, without the use of preservatives or antimicrobials such as benzethonium chloride.

The present invention relates to premixed pharmaceutical compositions of ketamine, or a pharmaceutically acceptable salt thereof, in an intravenous bag or other infusion container. The ready-to-use premixed pharmaceutical compositions of ketamine of the present invention are formulated for administration to a patient, without the need to reconstitute or dilute the composition prior to administration, e.g., in a ready-to-use infusion bag (also referred to as a "ready-to-use bag").

In one aspect, the ketamine product of the disclosure is a ready-to-use, sterile, infusion bag comprising an aqueous ketamine solution without benzethonium chloride comprising about 0.5 to about 2.5 mg/mL ketamine, a tonicity adjusting agent, a pH adjusting agent, and water for injection. In one aspect, the ketamine product is terminally sterilized. In one aspect, the ketamine product comprise a sterile aqueous ketamine solution that is aseptically filled, for example, the sterile aqueous ketamine solution is filled under aseptic conditions into a sterile infusion bag. In one aspect, the ketamine product of the disclosure is free of a preservative or antimicrobial such as benzethonium chloride.

In one aspect, the ready-to-use, sterile, infusion container comprising an aqueous ketamine solution without benzethonium chloride comprises ketamine at a concentration of about 1 to about 2 mg/mL. In certain aspects, the pharmaceutically acceptable salt is ketamine hydrochloride. In certain aspects, the tonicity adjustment agent comprises sodium chloride.

In one aspect, the pH adjusting agent comprises hydrochloric acid, sodium hydroxide, or a combination thereof. In certain aspects, the pH of the aqueous ketamine solution without benzethonium chloride is about 3 to 6. In certain aspects, the pH of the aqueous ketamine solution without benzethonium chloride is about 3.5 to 5.5.

In one aspect, the liquid pharmaceutical composition is free of a preservative. In certain aspects, the preservative-free aqueous ketamine solution is free of a chelating agent, an antioxidant, a stabilizer, and a complexing agent. In certain aspects, the aqueous ketamine solution is antimicrobial-free (e.g., free of benzethonium chloride), but may contain one or more chelating agents, complexing agents, stabilizers, and/or antioxidants.

In one aspect, the aqueous ketamine solution has an osmolality of about 270-330 mOsmol/kg. In certain aspects, the aqueous ketamine solution is formulated as a total volume of about 50-500 mL.

In one aspect, the ready-to-use, sterile, infusion bag comprising aqueous ketamine solution without benzethonium chloride comprises at least one port. In one aspect, the ready to use terminally sterilized infusion bag comprising a aqueous ketamine solution without benzethonium chloride comprises at least one tube port closed with a closure. In certain aspects, the closure is a twist off closure. In certain aspects, the tube port comprises a multilayer polyolefin and styrene block copolymer tube material. In certain aspects, the twist off closure comprises a membrane that creates a barrier, splitting the twist-off closure in two parts. In certain aspects, the twist off closure comprises an inferior part of the membrane in direct contact with the ketamine solution, while the superior part is in contact with a zone that forms an air chamber into the closure as illustrated in FIG. 8. In certain aspects, the twist off closure comprises at least one layer of polypropylene. In certain aspects, the closure is a rubber stopper. In certain aspects, the twist off closure comprises at least one layer of polyethylene. In certain aspects, the closure comprises a plastic material. In certain aspects, the closure is a cap. Other closure systems that are stable, with low leachables, and without physical deformation during terminal sterilization are also contemplated in this disclosure. In certain aspects, the tube port comprises at least one layer of block copolymer. In certain aspects, the tube port comprises multiple layers of a block copolymer. In certain aspects, the tube port comprises multiple layers of a polyolefin block copolymer. In certain aspects, the tube port comprises one or more layers of a plastic material.

In one aspect, the infusion bag comprises a flexible film. In certain aspects, the film is a flexible multilayer film. In some aspects, the innermost layer of the infusion container is made-up of a material that shows minimal or no adsorption of ketamine thereby causing no loss of potency and/or assay percentage during preparation, filling, sterilization and during storage. In some aspects, the multilayer film may comprise other layers that may be made up of materials such as polyethylene, polypropylene, modified polyolefin-polyethylene polymers, styrene-polyolefin based polymers and block co-polymers thereof etc. In certain aspects, the infusion bag comprises a flexible multilayer film comprising polyolefin and styrene-ethylene-butylene (SEB) block copolymer. In certain aspects, the infusion bag comprises a flexible multilayer polypropylene styrene-block copolymer based film. In certain aspects, the infusion bag comprises 2 to 5 layers of polypropylene styrene-block copolymer based film. In certain aspects, the infusion bag comprises a 3-layer polypropylene styrene-block copolymer based film. In certain aspects, the infusion bag comprises a flexible multilayer film in which certain layers are comprised of different polymers or polymer blends from other layers. In one aspect, the infusion bag comprises a flexible film. In certain aspects, the film is a flexible single layer film.

In one aspect, the primary packaging for the ready-to-use, sterile, aqueous ketamine solution without benzethonium chloride is a flexible intravenous bag. In one aspect, the primary packaging for the ready-to-use, sterile, aqueous ketamine solution without benzethonium chloride is a pre-filled syringe. In one aspect, the primary packaging for the ready-to-use, sterile, aqueous ketamine solution without benzethonium chloride is a glass container. In one aspect, the primary packaging for the ready-to-use terminally sterilized aqueous ketamine solution without benzethonium chloride is a plastic bottle or semi-flexible IV container.

In one aspect, the infusion container may be enclosed in an overwrap. In certain aspects, the overwrap comprises polyester, aluminum, polypropylene, or a combination thereof. In certain aspects, the overwrap comprises four layers comprising polyester, aluminum, polypropylene, and polyester.

In one aspect, the ready-to-use infusion container comprising an aqueous ketamine solution without benzethonium chloride is terminally sterilized by autoclaving. In one aspect, the ready-to-use infusion container comprising an aqueous ketamine solution without benzethonium chloride is terminally sterilized using steam sterilization. In one aspect, the ready-to-use infusion container comprising an aqueous ketamine solution without benzethonium chloride is terminally sterilized using heat sterilization. In one aspect, the ready-to-use infusion container comprising a aqueous ketamine solution without benzethonium chloride is terminally sterilized by radiation. In one aspect, the ready-to-use, infusion container comprising a aqueous ketamine solution without benzethonium chloride is terminally sterilized by chemical sterilization (e.g., ethylene oxide).

In one aspect, the ketamine product in a ready-to-use, sterile container comprising an aqueous ketamine solution without benzethonium chloride has a shelf-life of greater than three months at room temperature. In some aspects, the ketamine product in a ready-to-use, sterile container comprising an aqueous ketamine solution without benzethonium chloride has a shelf-life of greater than six months, greater than twelve months, greater than eighteen months, or greater than twenty-four months at room temperature. In one aspect, the ketamine or a pharmaceutically acceptable salt thereof in a ready-to-use, sterile infusion container comprising an aqueous ketamine solution without benzethonium chloride of the disclosure is chemically stable for at least 24 months when stored at a controlled room temperature. In certain aspects, the controlled room temperature is 15-30° C. In certain aspects, the ketamine or a pharmaceutically acceptable salt thereof is chemically stable for at least 24 months at 25° C.±2° C. with relative humidity (RH) at 40%±5% when stored in the ready-to-use, terminally sterilized, infusion container.

In one aspect, the average number of particles equal to or greater than 10 μm present in the aqueous ketamine solution without benzethonium chloride of the disclosure units tested does not exceed 6000 per container when the terminally sterilized infusion bag comprising an aqueous ketamine solution without benzethonium chloride is stored at room temperature for at least 24 months. In one aspect, the average number of particles equal to or greater than 10 μm present in the aqueous ketamine solution without benzethonium chloride of the disclosure units tested does not exceed 600 per container. In one aspect, the average number of particles equal to or greater than 10 μm present in the aqueous ketamine solution without benzethonium chloride of the disclosure units tested does not exceed 60 per container. In certain aspects, the average number of particles equal to or greater than 25 μm present in the units tested does not exceed 600 per container when the terminally sterilized infusion bag comprising an aqueous ketamine solution without benzethonium chloride is stored at room temperature for at least 24 months.

In one aspect, the impurities in the ready-to-use, sterile, infusion bag comprising a aqueous ketamine solution without benzethonium chloride total not more than 1%, not more than 0.4%, not more than 0.3%, not more than 0.2%, not more than 0.15%, or not more than 0.05%, or not more than 0.01%.

In one aspect, the ketamine content of the sterile, aqueous ketamine solution without benzethonium chloride of the disclosure after accelerated storage at 40° C.±2° C./<25% RH for 6 months is greater than 98%, greater than 99%, or greater than 99.5%, or greater than 99.9%, or greater than 99.95%.

In one aspect, the bacterial endotoxin in the aqueous ketamine solution without benzethonium chloride of the disclosure is about 0.4 EU/mg. In one aspect, the bacterial endotoxin in the sterile, aqueous ketamine solution without benzethonium chloride of the disclosure is less than about 0.4 EU/mg, less than about 0.3 EU/mg, less than about 0.2 EU/mg, or less than about 0.1 EU/mg.

In one aspect, the ketamine content of the sterile, aqueous ketamine solution without benzethonium chloride of the disclosure after long-term storage for 12 months at 25° C.±2° C./40% RH±5% RH is 99% or greater. In one aspect, the ketamine content of the sterile, aqueous ketamine solution without benzethonium chloride of the disclosure after long-term storage for 12 months at 25° C.±2° C./40% RH±5% RH is 99.5% or greater. In one aspect, the ketamine content of the sterile, aqueous ketamine solution without benzethonium chloride of the disclosure after long-term storage for 18 months at 25° C.±2° C./40% RH±5% RH is 99% or greater. In one aspect, the ketamine content of the sterile, aqueous ketamine solution without benzethonium chloride of the disclosure after long-term storage for 18 months at 25° C.±2° C./40% RH±5% RH is 99.5% or greater. In one aspect, the ketamine content of the sterile, aqueous ketamine solution without benzethonium chloride of the disclosure after long-term storage for 24 months at 25° C.±2° C./40% RH±5% RH is 99% or greater.

In one aspect, the present invention includes a method of preparing the ready-to-use, terminally sterilized, infusion bag comprising a aqueous ketamine solution without benzethonium chloride of the disclosure, comprising: (i) adding ketamine or a pharmaceutically acceptable salt thereof to water; (ii) adjusting the pH to about 3.5 to 5.5 using a pH adjusting agent; (iii) filtering the solution of step (ii); (iv) filling the solution into an infusion bag, for example, through the tube port; (v) terminally sterilizing the infusion bag of step (iv); (vii) overwrapping the terminally sterilized infusion bag of step (vi) with an overwrap. In certain aspects, the terminal sterilization is conducted by autoclaving. In certain aspects, said autoclaving is at a temperature ranging from 110 to 130° C. for a period of time ranging from 7 to 60 minutes. In certain aspects, said autoclaving is at a temperature of 121° C. for a period of time ranging from 7 to 60 minutes. In certain aspects, said autoclaving is at a temperature of 121° C. for about 15 minutes. In certain aspects, no glue is used to seal the tube port to the film or the closure to the tube port; autoclave heat ensures a hermetic seal between the tube port and the film and the tube port and closure.

In one aspect, the present invention includes a method of treating a subject in need of analgesia, comprising administering the ketamine solution from the ready-to-use, sterile infusion bag to the subject without diluting the ketamine solution; and wherein the ketamine is administered as a continuous infusion. In certain aspects, the ketamine solution is administered by an intravenous infusion.

In one aspect, the subject is in need of anesthesia for a diagnostic or a surgical procedure. In certain aspects, the subject is in need of anesthesia prior to administration of an anesthetic agent other than ketamine or a pharmaceutically acceptable salt thereof.

In one aspect, the subject is in need of ketamine administration in addition to administration of an anesthetic agent other than ketamine or a pharmaceutically acceptable salt thereof.

DETAILED DESCRIPTION

Figure 1:
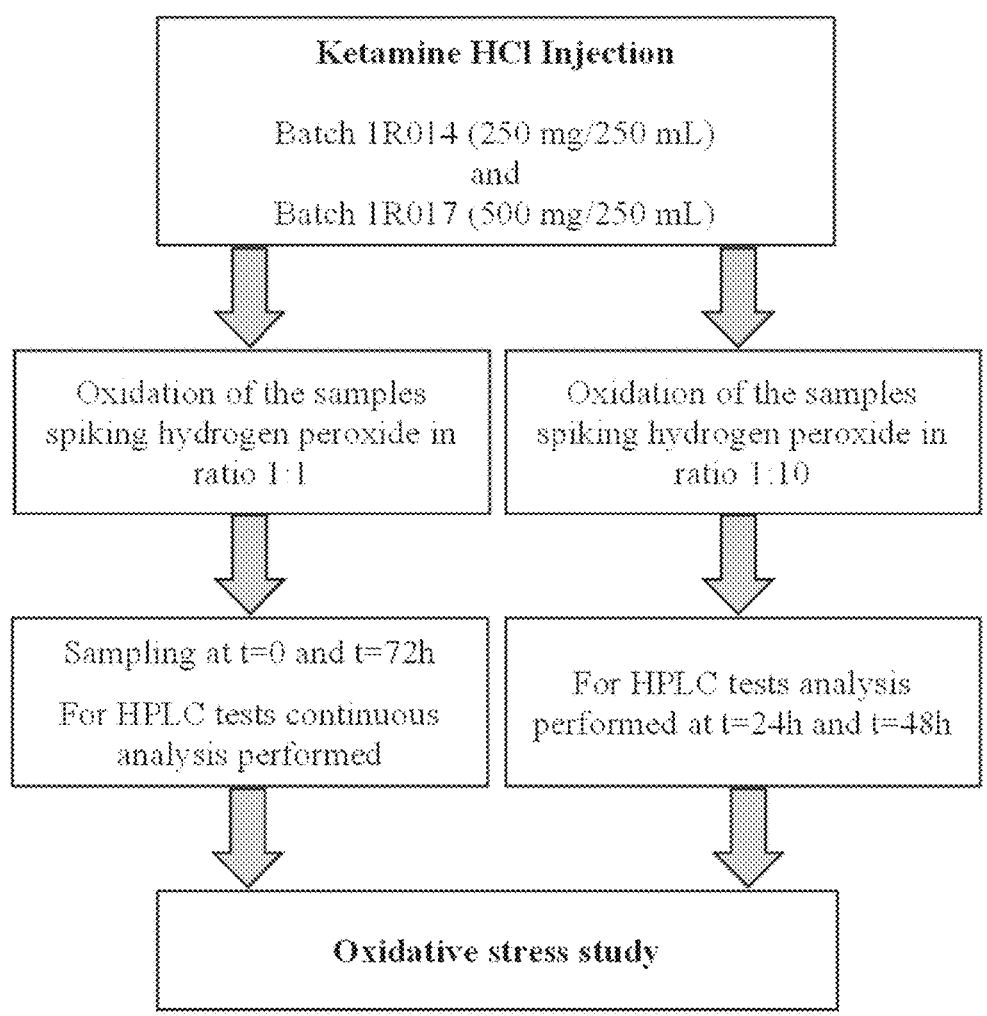
FIG. 1 shows the steps and specifications of the oxidative stress study conducted on the ready to use sterile infusion bag comprising a preservative-free aqueous ketamine solution of the disclosure ("ketamine product of the disclosure"). Two batches of ketamine HCL injection (1R014 and 1R017) at two different concentrations (1 mg/mL and 2 mg/mL respectively) were spiked with hydrogen peroxide at different ratios (1:1 and 1:10). HPLC tests were performed to determine the effects of oxidative stress on the ketamine HCL injection product.

The present invention includes ketamine prepared in a premixed, ready to use, formulation that does not require reconstitution or dilution prior to administration to a patient. In one aspect, the ketamine product of the disclosure is terminally sterilized in an infusion container with high integrity, and remains stable and active after prolonged storage. In another aspect, the ketamine product of the disclosure is produced under aseptic conditions. Such premixed formulations therefore avoid the cost, inconvenience, and risk of contamination or overdose that can be associated with reconstituting or diluting a concentrated ketamine formulation prior to administration to a patient. The present invention includes ready-to-use ketamine formulations that do not comprise a preservative, or that do not contain an antimicrobial such as benzethonium chloride, but remain sterile and stable when stored at room temperature for a prolonged period (e.g., 24 months) in a sterile infusion container.

The present invention relates to premixed pharmaceutical compositions of ketamine, or a pharmaceutically acceptable salt thereof, in an infusion container. The premixed pharmaceutical compositions of ketamine of the present invention are formulated for administration to a patient, without the need to reconstitute or dilute the composition prior to administration, and remain active after prolonged storage.

In one aspect, the present invention of the disclosure is a ready-to-use, sterile infusion container comprising an aqueous ketamine solution without benzethonium chloride comprising about 0.5 to about 2.5 mg/mL ketamine, a tonicity adjusting agent, a pH adjusting agent, and water for injection.

In certain aspects, the ready-to-use, sterile infusion container comprising an aqueous ketamine solution without benzethonium chloride comprises ketamine at a concentration of about 1 to about 2 mg/mL. In certain aspects, the pharmaceutically acceptable salt is ketamine hydrochloride. In certain aspects, the tonicity adjustment agent comprises sodium chloride.

In certain aspects, the pH adjusting agent comprises hydrochloric acid, sodium hydroxide, or a combination thereof. In certain aspects, the pH of the aqueous ketamine solution is about 3 to 6. In certain aspects, the pH of the aqueous ketamine solution is about 3.5 to 5.5.

In certain aspects, the liquid pharmaceutical composition is free of a preservative. In certain aspects, the preservative-free aqueous ketamine solution is free of a chelating agent, an antioxidant, a stabilizer, a complexing agent and a preservative. In certain aspects, the aqueous ketamine solution is antimicrobial-free (e.g., free of benzethonium chloride), but may contain one or more chelating agents, complexing agents, stabilizers, and/or antioxidants.

In certain aspects, the preservative-free or antimicrobial-free aqueous ketamine solution has an osmolality of about 270-330 mOsmol/kg. In certain aspects, the aqueous ketamine solution without benzethonium chloride is formulated as a total volume of about 50-500 mL.

In one aspect, the primary packaging for the ready-to-use, sterile aqueous ketamine solution without benzethonium chloride is an intravenous bag. In one aspect, the primary packaging for the ready-to-use, sterile, aqueous ketamine solution without benzethonium chloride is a pre-filled syringe. In one aspect, the primary packaging for the ready-to-use, sterile, aqueous ketamine solution without benzethonium chloride is a glass container. In one aspect, the primary packaging for the ready-to-use, sterile, aqueous ketamine solution without benzethonium chloride is a plastic bottle or semi-flexible IV container.

In one aspect, the intravenous bag is made up of multilayer polypropylene styrene-block copolymer. Such containers are available commercially under the APP-series film IV bag products manufactured by Polycine, such as APP-114S. In one aspect, the intravenous bag comprises an inner layer made up of a cycloolefin polymer, a middle layer made up of linear low density polyethylene polymer and an outer layer made up of low density polyethylene polymer. Such containers are available commercially available as Polyelite EHC® film bags manufactured by Hosokawa. In another aspect, intravenous bag is made up of an outer layer of polypropylene polymer with styrene-ethylene-butylene (SEB) block copolymer and a middle and inner layer made up of polypropylene based polyolefin polymer with styrene-ethylene butylene block copolymer. Such containers are available commercially under the brand name Inerta 103 and are manufactured by Technoflex. In another aspect, the intravenous bag is made up of multilayer polyolefin film. Such containers are available as Nexcel brand M312 and M312A® films by SealedAir Corporation, and as M312 films from other manufacturers. Other commercially-available intravenous bags that are stable, with low leachables, and without physical deformation during terminal sterilization are also contemplated in this disclosure. In one aspect, the infusion bag comprises a single layer of flexible film.

In one aspect, the primary packaging for the ready-to-use, sterile, aqueous ketamine solution without benzethonium chloride is an infusion container. In certain aspects, the infusion container is a flexible infusion bag. In certain aspects, the infusion bag comprises at least one port. In certain aspects, the infusion container is a prefilled syringe. In certain aspects, the infusion container is a glass container. In certain aspects, the infusion container is a semi-flexible plastic infusion container.

In one aspect, the ready to use, sterile infusion bag, comprising an aqueous ketamine solution without benzethonium chloride comprises at least one port. In some aspects, the port is a tube port closed with a closure. In certain aspects, the tube port comprises a multilayer polyolefin and styrene block copolymer tube material. In certain aspects, the tube port comprises at least one layer of block copolymer. In certain aspects, the tube port comprises multiple layers of a block copolymer. In certain aspects, the tube port comprises multiple layers of a polyolefin block copolymer at least one port is a tube port. In certain aspects, the tube port comprises one or more layers of a plastic material.

In some aspects, the tube port comprises a PP/EVA material. In some aspects, the tube port comprises a multi-layer co-extruded connector tubing. In some aspects, the tube port is PVC-free and/or plasticizer free. In some aspects, the tubing port is sealed closed. Other polymers that are stable, with low leachables, and without physical deformation during terminal sterilization may also be used for the port.

In certain aspects the closure is a twist-off closure. In certain aspects, the closure comprises a membrane that creates a barrier, splitting the closure in two parts. In certain aspects, the closure comprises an inferior part of the membrane in direct contact with the ketamine solution, while the superior part is in contact with a zone that forms an air chamber into the closure. In certain aspects, the closure comprises at least one layer of polypropylene. In certain aspects, the closure comprises at least one layer of polyethylene. In certain aspects, the closure comprises at least one layer of polypropylene. In certain aspects, other polymers that are stable, with low leachables, and without physical deformation during terminal sterilization may also be used for the closure.

In certain aspects, the port may have a stopper, such as a rubber stopper, to provide a fluid tight closure of the passage and a lid member that clamps the periphery of the stopper. In certain aspects, the port may have a stopper comprising a plastic material. In a non-limiting embodiment, the port may have a resalable stopper which provides fluid tight closure of the passage and a plastic cap that clamps the periphery of the resealable stopper. Other closure systems that are stable, with low leachables, and without physical deformation during terminal sterilization are also contemplated in this disclosure. In a non-limiting embodiment, the port may be a resealable twist off port, which may also be referred to as a "spike port." In some embodiments, the infusion container of the present invention may optionally be overwrapped by an overwrap pouch covering the filled and sealed infusion container. In some embodiments, the infusion container is overwrapped by an aluminum pouch, which may further comprise other materials or a combination of other materials, for example, a four layer overwrap. The present invention does not relate to semi-solid topical formulations (such as gel, hydrogel, emulgel, paste, cream, ointment etc.), inhalations or aerosols and/or non-aqueous formulations that are not suitable for parenteral administration.

In one aspect, the infusion bag comprises a flexible film. In some aspects, the flexible film may be a multilayer film or a single layer film. In some aspects, the innermost layer of the infusion container is made-up of a material that shows minimal or no adsorption of ketamine thereby causing no loss of potency and/or assay percentage during preparation, sterilization and during storage. In some aspects, the multilayer film may comprise other layers that may be made up of materials such as polyethylene, polypropylene, modified polyolefin-polyethylene polymers, styrene-polyolefin based polymers and block co-polymers thereof, etc. In certain aspects, the infusion bag comprises a flexible multilayer film comprising polyolefin and styrene-ethylene-butylene (SEB) block copolymer. In certain aspects, the infusion bag comprises a multilayer polypropylene styrene-block copolymer based film. In certain aspects, the infusion bag comprises 2 to 5 layers of polypropylene styrene-block copolymer based film. In certain aspects, the infusion bag comprises a 3-layer polypropylene styrene-block copolymer based film. In one aspect, the infusion bag comprises a flexible multilayer film comprising a multilayer polyolefin film. In some aspects the infusion bag comprises 2 to 7 layers of polyolefin film. In some aspects, the infusion bag comprises a 5 layer polyolefin film. In some aspects, the flexible film may be a multilayer film or a single layer film. In some aspects, the film may be an M312 film, such as Nexcel brand M312A film manufactured by SealedAir Corporation; an M315 film manufactured by SealedAir Corporation; an APP-series film manufactured by Polycine, such as APP-114S film manufactured by Polycine; a polypropylene film, such as those manufactured by Technoflex, such as an Inerta® film manufactured by Technoflex; a cycloolefin polymer with a middle layer made up of linear low density polyethylene polymer and an outer layer made up of low density polyethylene polymer, such as those manufactured by Hosokawa; an Inerta 103 film, made up of an outer layer of polypropylene polymer with styrene-ethylene-butylene (SEB) block copolymer and a middle and inner layer made up of polypropylene based polyolefin polymer with styrene-ethylene butylene block copolymer, which may be manufactured by Technoflex; or another commercially-available polymer film designed for use in intravenous bag products. In certain aspects, other polymers that are stable, with low leachables, and without physical deformation during terminal sterilization may also be used for the infusion bag.

In certain aspects, the infusion container (e.g., infusion bag) is contained in an overwrap. In certain aspects, the overwrap comprises polyester, aluminum, polypropylene, or a combination thereof. In certain aspects, the overwrap comprises four layers comprising polyester, aluminum, polypropylene, and polyester.

Aseptic processing involves sterile filtration and aseptic processing of a pharmaceutical product, wherein a premixed pharmaceutical solution is sterilized, for example, by filtering a pharmaceutical solution through a pre-filter with a filter absolute rating: 0.45 µm followed by a filtration through two sterilizing filters (0.2 µm pore size filters) under aseptic conditions, or similar conditions. The filtration can be pressure driven (conducted under compressed air). Aseptic filling of the sterile solution into a sterile container can be achieved, for example, by filling the pre-sterilized bag in line with filtration under aseptic conditions. After filling, port of the infusion bags used for product solution filling can be sealed.

Terminal sterilization involves sterilizing a pharmaceutical product in its sealed final container (e.g., in an infusion bag). A sterilizing agent or process is used to kill microbes and other pathogens to create a sterile final product. Terminal sterilization of ketamine formulations in infusion bags can be achieved by steam sterilization, heat sterilization, such as an autoclave method or any other methods known in the art; by radiation treatment such as Gamma, E-beam or ultraviolet; or by chemical sterilization, e.g., ethylene oxide. See, e.g., U.S. Pat. Nos. 5,439,643 and 8,617,467, each incorporated herein by reference in their entireties. Heat sterilization may include steam sterilization and autoclaving. A terminally sterilized drug product undergoes final sterilization in a sealed container, and thus, enhances safety by reducing the risk of contamination. Terminal sterilization is one of the most difficult requirements for medical devices. It eliminates viable pathogens (e.g., microbes and viruses) to produce a sterile final product, but it involves conditions that can affect the integrity of the packaging, cause leaching of packaging components into the pharmaceutical solution, cause degradation of the drug product, and/or otherwise affect the stability the pharmaceutical solution. Every component of an infusion bag that is subjected to terminal sterilization (including the bag film, ports, and closures) must be able to withstand terminal sterilization conditions and must be compatible with the pharmaceutical solution components under those conditions.

In certain aspects, the terminal sterilization procedure of the ready to use terminally sterilized infusion container comprising a preservative-free or antimicrobial-free aqueous ketamine solution of the disclosure is autoclaving. Autoclaving involves application of elevated temperature and/or pressure to achieve sterilization. Other methods of terminal sterilization (e.g., ethylene oxide, radiation) also involve harsh conditions. Subjecting a pharmaceutical composition in a final container to terminal sterilization can adversely affect the pharmaceutical composition, the material of the final container, and the sealing integrity of the final container. Thus, not all pharmaceutical compositions and final containers are mutually suitable for terminal sterilization using heat sterilization. Heat sterilization may be performed using steam, preferably wet steam, or superheated water. The time period for the sterilization must be long enough to meet the sterility requirements required of an injectable product. When steam is used the period may be from about 5 to 30 minutes at temperatures of about 110° C. to 130° C., or from about 10 to 30 minutes at temperatures of about 110° C. to 130° C., preferably at 120° C. to 125° C. for 15 to 30 minutes. In another aspect, the sterilization can be at 120° C. for 15 to 20 minutes. The pharmaceutical formulation should be analyzed after sterilization for the presence of leachables and other impurities.

In certain aspects, the ketamine or a pharmaceutically acceptable salt thereof in a ready-to-use, sterile infusion container comprising a preservative-free or antimicrobial-free aqueous ketamine solution of the disclosure is chemically stable for at least 24 months when stored at a controlled room temperature. In certain aspects, the controlled room temperature is 15-30° C. In certain aspects, the ketamine or a pharmaceutically acceptable salt thereof is chemically stable for at least 24 months at 25° C.±2° C. with relative humidity (RH) at 40%±5% when stored in the ready-to-use, terminally sterilized, infusion container. In certain aspects, the ketamine or a pharmaceutically acceptable salt thereof is chemically stable for at least 24 months at 25° C.±2° C. with relative humidity (RH) at 40%±5% when stored in the ready-to-use, sterile, infusion container.

In certain aspects, the average number of particles equal to or greater than 10 μm present in the preservative-free or antimicrobial-free aqueous ketamine solution of the disclosure units tested does not exceed 6000 per container when the sterile infusion bag comprising a preservative-free or antimicrobial-free aqueous ketamine solution is at room temperature for at least 24 months. In one aspect, the average number of particles equal to or greater than 10 μm present in the preservative-free or antimicrobial-free aqueous ketamine solution does not exceed 600 per container. In one aspect, the average number of particles equal to or greater than 10 μm present in the preservative-free or antimicrobial-free aqueous ketamine solution does not exceed 60 per container. In certain aspects, the average number of particles equal to or greater than 25 μm present in the units tested does not exceed 600 per container when the terminally sterilized infusion bag comprising a preservative-free or antimicrobial-free aqueous ketamine solution is at room temperature for at least 24 months. In certain aspects, the preservative-free or antimicrobial-free aqueous ketamine solution of the disclosure comprises contains not more than 23, e.g., 0 to 23, 0 to 15, 0 to 10, 0 to 5, 0 to 4, 0 to 3, 0 to 2, 0 to 1, or 0 particulates greater than or equal to 10 microns in size. In certain aspects, the preservative-free or antimicrobial-free aqueous ketamine solution of the disclosure comprises contains not more than 3, e.g., 0 to 3, 0 to 2, 0 to 1, or 0 particulates greater than or equal to 25 microns in size.

In certain aspects, the impurities in the ready-to-use, sterile infusion container comprising an aqueous ketamine solution without benzethonium chloride are less than or equal to 1%. In certain aspects, the impurities in the ready-to-use, sterile infusion container comprising an aqueous ketamine solution without benzethonium chloride are not more than 2%, not more than 1.5%, not more than 1%, not more than 0.5%, not more than 0.2%, not more than 0.15%, or not more than 0.05%.

In one aspect, the ketamine content of the sterile, aqueous ketamine solution without benzethonium chloride of the disclosure after accelerated storage at 40° C.±2° C./<25% RH for 6 months is greater than 99.5%. In one aspect, the ketamine content of the sterile, aqueous ketamine solution without benzethonium chloride of the disclosure after accelerated storage at 40° C.±2° C./<25% RH for 6 months is greater than 99%. In one aspect, the ketamine content of the sterile, aqueous ketamine solution without benzethonium chloride of the disclosure after accelerated storage at 40° C.±2° C./<25% RH for 6 months is greater than 98.5%. In one aspect, the ketamine content of the sterile, aqueous ketamine solution without benzethonium chloride of the disclosure after accelerated storage at 40° C.±2° C./<25% RH for 6 months is greater than 98%. In one aspect, the ketamine content of the sterile, aqueous ketamine solution without benzethonium chloride of the disclosure after accelerated storage at 40° C.±2° C./<25% RH for 6 months is greater than 97.5%. In one aspect, the ketamine content of the sterile, aqueous ketamine solution without benzethonium chloride of the disclosure after accelerated storage at 40° C.±2° C./<25% RH for 6 months is greater than 97%.

In certain aspects, the bacterial endotoxin in the aqueous ketamine solution without benzethonium chloride of the disclosure is about 0.4 EU/mg. In certain aspects, the bacterial endotoxin in the aqueous ketamine solution without benzethonium chloride of the disclosure is less than about 0.4 EU/mg, for example, less than about 0.3 EU/mg, less than about 0.2 EU/mg, or less than about 0.1 EU/mg.

In one aspect, the ketamine content of the sterile, aqueous ketamine solution without benzethonium chloride of the disclosure after long-term storage for 12 months at 25° C.±2° C./40% RH±5% RH is 99.5% or greater. In one aspect, the ketamine content of the sterile, aqueous ketamine without benzethonium chloride solution of the disclosure after long-term storage for 12 months at 25° C.±2° C./40% RH±5% RH is 99% or greater. In one aspect, the ketamine content of the sterile, aqueous ketamine solution without benzethonium chloride of the disclosure after long-term storage for 12 months at 25° C.±2° C./40% RH±5% RH is 99.9% or greater. In one aspect, the ketamine content of the sterile, aqueous ketamine solution without benzethonium chloride of the disclosure after long-term storage for 12 months at 25° C.±2° C./40% RH±5% RH is 98.5% or greater. In one aspect, the ketamine content of the sterile, aqueous ketamine solution without benzethonium chloride of the disclosure after long-term storage for 12 months at 25° C.±2° C./40% RH±5% RH is 98% or greater. In one aspect, the ketamine content of the sterile, aqueous ketamine solution of the disclosure after long-term storage for months at 25° C.±2° C./40% RH±5% RH is 97.5% or greater. In one aspect, the ketamine content of the sterile, aqueous ketamine solution without benzethonium chloride of the disclosure after long-term storage for 12 months at 25° C.±2° C./40% RH±5% RH is 97% or greater.

In one aspect, the ketamine content of the sterile, aqueous ketamine solution without benzethonium chloride of the disclosure after long-term storage for 18 months at 25°

C.±2° C./40% RH±5% RH is 99% or greater. In one aspect, the ketamine content of the sterile, aqueous ketamine solution without benzethonium chloride of the disclosure after long-term storage for 18 months at 25° C.±2° C./40% RH±5% RH is 98.5% or greater. In one aspect, the ketamine content of the sterile, aqueous ketamine solution without benzethonium chloride of the disclosure after long-term storage for 18 months at 25° C.±2° C./40% RH±5% RH is 98% or greater. In one aspect, the ketamine content of the sterile, aqueous ketamine solution without benzethonium chloride of the disclosure after long-term storage for 18 months at 25° C.±2° C./40% RH±5% RH is 97.5% or greater. In one aspect, the ketamine content of the sterile, aqueous ketamine solution without benzethonium chloride of the disclosure after long-term storage for 18 months at 25° C.±2° C./40% RH±5% RH is 97% or greater.

In one aspect, the ketamine content of the sterile, aqueous ketamine solution without benzethonium chloride of the disclosure after long-term storage for 24 months at 25° C.±2° C./40% RH±5% RH is 99% or greater. In one aspect, the ketamine content of the sterile, aqueous ketamine solution without benzethonium chloride of the disclosure after long-term storage for 24 months at 25° C.±2° C./40% RH±5% RH is 98.5% or greater. In one aspect, the ketamine content of the sterile, aqueous ketamine solution without benzethonium chloride of the disclosure after long-term storage for 24 months at 25° C.±2° C./40% RH±5% RH is 98% or greater. In one aspect, the ketamine content of the sterile, aqueous ketamine solution without benzethonium chloride of the disclosure after long-term storage for 24 months at 25° C.±2° C./40% RH±5% RH is 97.5% or greater. In one aspect, the ketamine content of the sterile, aqueous ketamine solution without benzethonium chloride of the disclosure after long-term storage for 24 months at 25° C.±2° C./40% RH±5% RH is 97% or greater.

In one aspect, the present invention includes a method of preparing the ready-to-use, terminally sterilized infusion bag comprising a aqueous ketamine solution without benzethonium chloride of the disclosure, comprising: (i) adding ketamine or a pharmaceutically acceptable salt thereof to water; (ii) adjusting the pH to about 3.5 to 5.5 using a pH adjusting agent; (iii) filtering the solution of step (ii); (iv) filling the solution into an infusion bag, for example, through the tube port; (v) terminally sterilizing the infusion bag of step (v); (vi) overwrapping the terminally sterilized infusion bag of step (v) with an overwrap. In certain aspects, the terminal sterilization is autoclaving. In certain aspects, said autoclaving is at a temperature ranging from 110 to 130° C. for a period of time ranging from 7 to 60 minutes. In certain aspects, said autoclaving is at a temperature of 121° C. for a period of time ranging from 7 to 60 minutes. In certain aspects, said autoclaving is at a temperature of 121° C. for about 15 minutes. In certain aspects, no glue is used to seal the tube port to the film or the closure to the tube port; autoclave heat insures a hermetic seal between the tube port and the film and tube port and closure.

In one aspect, the present invention includes a method of treating a subject in need of analgesia, comprising administering the ketamine solution using the ready-to-use, sterile infusion bag to the subject; and wherein the ketamine is administered as a continuous infusion. In certain aspects, the ketamine solution is administered by an intravenous infusion.

In one aspect, the subject is in need of anesthesia for a diagnostic or a surgical procedure. In certain aspects, the subject is in need of anesthesia prior to administration of an anesthetic agent other than ketamine or a pharmaceutically acceptable salt thereof.

In one aspect, the subject is in need of ketamine administration in addition to administration of an anesthetic agent other than ketamine or a pharmaceutically acceptable salt thereof.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the present disclosure and how to make and use them.

As used herein, the term "ketamine" refers to (RS)-2-(2-chlorophenyl)-2-(methylamino)cyclohexanone as the free base or in the form of a pharmaceutically acceptable salt. A pharmaceutically acceptable salt of ketamine can include inorganic acid salts such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, and salicylic acid. In certain aspects, the ketamine salt is ketamine HCl. In other non-limiting embodiments, ketamine comprises the structure depicted below in Formula I:

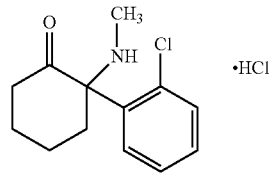 [SMILES: CNC1(c2ccccc2Cl)CCCCC1=O ; Cl]

Ketamine in aqueous solution has been shown to react under accelerated conditions of high temperature and pH by a process which involves initial formation of 1-[(2-chlorophenyl) (15ethylamino) methyl] cyclopentanol ("Compound A"). Thus, the term "Compound A" or "Impurity A" as used herein comprises the structure on the right-hand side of the reaction depicted below:

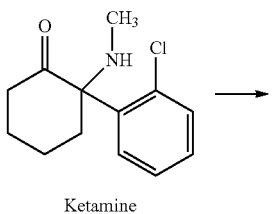
Ketamine

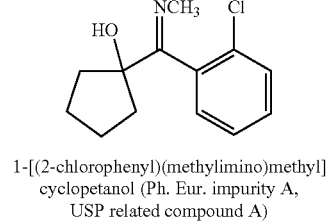
1-[(2-chlorophenyl)(methylimino)methyl] cyclopetanol (Ph. Eur. impurity A, USP related compound A)

Compound A, depending on temperature and pH, may then isomerize back to Ketamine or hydrolyze to the primary product of this reaction: (2-chlorophenyl)(1-hydroxycyclopentyl) methanone 2-(2-chlorophenyl)-2-hydroxycyclohexanone ("Impurity B") which may be major, although not primary product, that results from isomerization of (2-chlorophenyl)(1-hydroxycyclopentyl)methanone ("Impurity C"). The structures of "Compound A" (also referred to as "Impurity A"), "Impurity B," and "Impurity C," are depicted in the reaction below:

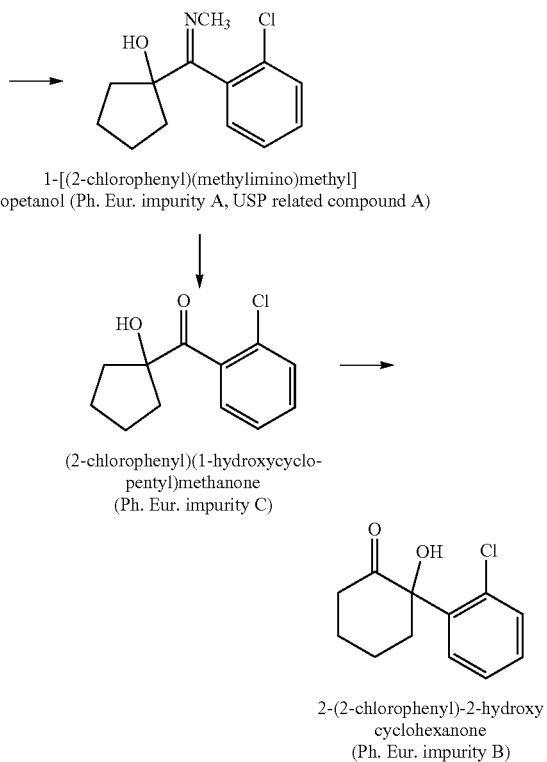

1-[(2-chlorophenyl)(methylimino)methyl]
cyclopetanol (Ph. Eur. impurity A, USP related compound A)

(2-chlorophenyl)(1-hydroxycyclo-
pentyl)methanone
(Ph. Eur. impurity C)

2-(2-chlorophenyl)-2-hydroxy
cyclohexanone
(Ph. Eur. impurity B)

The term, "chemically stable," as used herein, refers to a chemical compound which retains its chemical structure and useful properties on a timescale of its expected usefulness. Specifically, the usefulness of the compound is maintained in the environment in which it is stored. Conversely, a compound lacks chemical stability if it decomposes under the conditions of a specific environment. As used herein in certain embodiments, "chemically stable" may mean resistant to degradation of ketamine into its known or unknown decomposition elements. The level of ketamine identified impurity that is acceptable can be up to 0.15% of the formulation as per the ICH guidelines for shelf-life determination, but in certain preferred embodiments, the amount of impurities is lower, e.g., less than 0.05% of the formulation.

As used herein, the terms "premix", "premixed", or "premixture" refers to a pharmaceutical formulation that does not require reconstitution or dilution prior to administration to a patient. For example, in contrast to non-premixed formulations of ketamine, the premixed compositions provided herein are suitable for administration to a patient without dilution by, for example, a clinician, hospital personnel, caretaker, patient or any other individual.

As used herein, the term "ready-to-use" or "ready to use" refers to premixed compositions that are suitable for administration to a patient without further manipulation (e.g., a pharmaceutical formulation that is in the container from which the product is administered to the patient (such as an infusion bag or prefilled syringe) and does not require dilution or admixing before administration).

As used herein, the term "container closure system" refer to the sum of packaging components that together contain and protect the dosage form, including primary packaging components and secondary packaging components.

As used herein, the terms "primary packaging components," "primary packaging" means packaging components that are or may be in direct contact with the dosage form. For example, the primary packaging may be an infusion bag, including a flexible film component, one or more ports, and a closure system.

The terms "infusion bag," "intravenous bag," and "IV bag" may be used interchangeably herein and refer to a type of primary packaging, which comprises a bag film, port(s) and closure system(s). Such infusion bags may be used to administer intravenous infusion products.

The term "infusion container" as used herein refers to a type of primary packaging used to administer intravenous infusion products, for example, a flexible infusion bag, a semi-flexible plastic infusion container, a prefilled syringe, etc.

As used herein, the term "flexible" refers to a material that has the ability to deform and return to its original shape when the applied stress is removed without breaking or damage at around standard temperature and pressure (STP), for example about 0° C.±40° C. and 1 atm±0.005 atm. Flexible materials are distinguished from rigid materials such as glass. A "flexible" infusion bag allows fluid to drain out of the bag without venting. A "flexible" infusion bag may have port tubes and/or closures that are made of rigid or semi-rigid materials, provided that the bag film is flexible.

As used herein, the terms "secondary packaging components" and "overwrap" refer to a packaging component that is intended to provide additional protection to the drug product but is not typically in direct contact with the dosage form during storage.

As used herein, the terms "subject" or "patient" refer to a human, a non-human mammal or a non-human animal. The compounds and compositions of the present disclosure have application in veterinary medicine as well as for humans, e.g., for the treatment of domesticated species such as canine, feline, and various other pets; farm animal species such as bovine, equine, ovine, caprine, porcine, etc.; wild animals, e.g., in the wild or in a zoological garden; and avian species, such as chickens, turkeys, quail, songbirds, etc.

As used herein, the terms "pharmaceutical composition" or "pharmaceutical formulation" relates to compositions that can be formulated in any conventional manner using one or more pharmaceutically acceptable diluents or excipients. A "pharmaceutically acceptable" solvent, diluent or excipient, as used herein, means approved by a regulatory agency of the federal or a state government, or as listed in the U.S. Pharmacopoeia or other generally recognized pharmacopoeia for use in mammals, and more particularly in humans. Suitable components of pharmaceutical compositions are described in, for example, "Remington's Pharmaceutical Sciences" by Philip P. Gerbino, 21st Edition (or previous editions).

As used herein, the terms "therapeutically effective dose," "dose," "effective amount," and "therapeutically effective amount" refer to an amount sufficient to produce the desired effect, which can be readily determined according to standard good medical practice by those of skill in the art. In other non-limiting embodiments, a therapeutically effective dose or effective amount may be any amount that produces a response that a user (e.g., a clinician) will recognize as an effective response to the therapy. Thus, a therapeutically effective amount will generally be an amount that induces a desired effect, such as, for example, sedation or analgesia.

As used herein, the terms "about" and "approximately" mean+/−20% of the recited value, or within an acceptable error range for the particular value as determined by one of ordinary skill in the art, which will depend in part on how the value is measured or determined, i.e., the limitations of the measurement system.

As used herein, the terms "intensive care unit" or "ICU" refer to any setting that provides intensive care.

As used herein, the terms "port," "tubing port," or "port tube" refer to a connector which is sealed into the container portion of an infusion bag. An infusion bag may include one or more ports. The ports may include administrative and/or additive ports. The ports of the invention use commerciality available polymers, elastomers, etc. and can comprise one or more layers, which can withstand terminal sterilization. The ports may be coextruded.

As used herein, the term "closure" refers to a component that closes or seals a container. A closure provides an effective barrier against microbial contamination. In some aspects, the closure is a twist off closure. The closures referred to herein may comprise commerciality available polymers, elastomers, etc. and can comprise one or more layers, which can withstand terminal sterilization.

As used herein, singular forms, including the singular forms "a" "an" and "the", specifically also encompass the plural referents of the terms to which they refer unless the context clearly dictates otherwise. In addition, as used herein, unless specifically indicated otherwise, the word "or" is used in the "inclusive" sense of "and/or" and not the "exclusive" sense of "either/or".

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

Pharmaceutical Formulations

The compounds and compositions of the invention may be formulated as pharmaceutical compositions by admixture with pharmaceutically acceptable solvents and excipients. For example, suitable components of pharmaceutical compositions are described in, for example, "Remington's Pharmaceutical Sciences" by Philip P. Gerbino, 21st Edition (or previous editions). In certain non-limiting embodiments, the compounds or compositions are provided in a therapeutically effective amount to an animal, such as a mammal, preferably a human, in need of treatment therewith for inducing a sedative, anxiolytic, analgesic, or anesthetic effect.

In certain non-limiting embodiments, ketamine is formulated as a pharmaceutical composition, wherein the ketamine is the only therapeutically active ingredient present in the composition. In another non-limiting embodiments, ketamine is formulated as a pharmaceutical composition, wherein the ketamine is formulated in combination with at least one or more other therapeutically active ingredient. The formulation is suitable for parenteral administration, such as intravenous administration.

The pharmaceutical formulations suitable for injectable use, such as, for example, intravenous administration, include sterile aqueous solutions or dispersions and sterile powders for the extemporaneous preparation of sterile injectable solutions or dispersion. It can be stable under the conditions of manufacture and storage and can be preserved against the contaminating action of microorganisms such as bacteria and fungi. Solvents or dispersion mediums suitable for stable pharmaceutical formulations include, for example, water for injection (WFI), saline, aqueous dextrose, ethanol, polyol (for example, glycerol, propylene glycol, and polyethylene glycol, and the like), suitable mixtures thereof, and oils. In certain aspects, the solvent may be sterile WFI, 0.9% sodium chloride injection (normal saline), or 5% dextrose in water. The prevention of the action of microorganisms can be brought about by various antibacterial and antifungal agents, for example, parabens, chlorobutanol, phenol, benzyl alcohol, sorbic acid, and the like. Exposure to potential microorganisms such as bacteria, viruses, and fungi can also be prevented using terminal sterilization of prefilled parenteral pharmaceutical products and packages or aseptic processing throughout the manufacturing process of the ketamine product.

Pharmaceutical formulations may include isotonicity adjusting agents, for example, sugars or sodium chloride. Prolonged absorption of the injectable compositions can be brought about by the use in the compositions of agents delaying absorption, for example, aluminum monostearate and gelatin. Sterile injectable solutions may be prepared by incorporating the ketamine in the required amounts in the appropriate solvent with various of the other ingredients enumerated above, as required, followed by filtering and/or terminal sterilization.

Pharmaceutical formulations may include one or more excipients. Pharmaceutically acceptable excipients which may be included in the formulation are buffers such as citrate buffer, phosphate buffer, acetate buffer, and bicarbonate buffer; amino acids; urea; alcohols; ascorbic acid; phospholipids; proteins, such as serum albumin, collagen, and gelatin; salts such as EDTA or EGTA, and sodium chloride; liposomes; polyvinylpyrrolidone; sugars, such as dextran, mannitol, sorbitol, and glycerol; propylene glycol and polyethylene glycol (e.g., PEG-4000, PEG-6000); glycerol; glycine; lipids; preservatives; suspending agents; stabilizers; and dyes. The term "stabilizer" refers to a compound optionally used in the pharmaceutical compositions of the present invention in order to increase storage life. Non-limiting examples of stabilizers include antioxidants. Buffer systems for use with the formulations include citrate; acetate; bicarbonate; and phosphate buffers.

Pharmaceutical formulations may include a non-ionic surfactant. Preferred non-ionic surfactants include Polysorbate 20, Polysorbate 80, Triton X-100, Triton X-114, Nonidet P-40, Octyl α-glucoside, Octyl β-glucoside, Brij 35, Pluronic, and Tween 20.

Methods of Using Ready to Use Ketamine Compositions

As noted above, the methods of treatment of the invention are directed to methods of analgesia in a patient in need thereof comprising administration of ketamine to the patient, wherein the ketamine is administered in an amount effective to produce the desired effect.

The ketamine for use in the invention can be administered via any suitable route. In a non-limiting embodiment, the therapeutic compound can be delivered in a controlled or sustained release system. For example, a compound or composition may be administered using intravenous infusion, continuous infusion, or other modes of administration. In certain non-limiting embodiments, the dosage of ketamine can be individualized and titrated to the desired clinical effect.

The present disclosure includes the following non-limiting list of items:

1. A ketamine product comprising an aqueous ketamine solution comprising about 0.5 to about 2.5 mg/mL ketamine, a tonicity adjusting agent, a pH adjusting agent, and water for injection, wherein the ketamine solution is free of benzethonium chloride, and wherein the ketamine product is sterile and ready-to-use (RTU).
2. The ketamine product of item 1, wherein the ketamine product has been terminally sterilized.
3. The ketamine product of any preceding item, wherein the ketamine is at a concentration of about 1 mg/mL to about 2 mg/mL.
4. The ketamine product of any preceding item, wherein the aqueous ketamine solution is preservative-free or antimicrobial-free.
5. The ketamine product of any preceding item, wherein the tonicity adjustment agent comprises sodium chloride, dextrose, glycerine, mannitol, potassium chloride, or any combination thereof.
6. The ketamine product of any preceding item, wherein the aqueous ketamine solution comprises 0.9% sodium chloride.
7. The ketamine product of any preceding item, further comprising a pH adjusting agent.
8. The ketamine product of item 7 wherein the pH adjusting agent comprises hydrochloric acid, sodium hydroxide, or a combination thereof.
9. The ketamine product of any preceding item, wherein the pH of the aqueous ketamine solution is about 3 to 6.
10. The ketamine product of any preceding item, wherein the pH of the aqueous ketamine solution is about 3.5 to 5.5.
11. The ketamine product of any preceding item, wherein the aqueous ketamine solution is contained in an infusion bag comprising at least one port sealed with a closure.
12. The ketamine product of any preceding item, wherein the solution comprises one or more of a chelating agent, an antioxidant, a stabilizer, or a complexing agent.
13. The ketamine product of any preceding item, wherein the aqueous ketamine solution has an osmolality of about 270-330 mOsmol/kg.
14. The ketamine product of any preceding item, wherein aqueous ketamine solution is formulated as a total volume of about 50-500 mL.
15. The ketamine product of any one of items 11-14, wherein the at least one port comprises a plastic material.
16. The ketamine product of item 15, wherein the at least one port comprises a multilayer polyolefin and styrene block copolymer tube material.
17. The ketamine product of any one of items 11-16, wherein the closure comprises a plastic material.
18. The ketamine product of any one of items 11-17, wherein the closure is a twist-off closure and comprises a membrane that creates a barrier, splitting the twist-off closure in two parts.
19. The ketamine product of item 18, wherein the twist-off closure comprises an inferior part of the membrane in direct contact with the ketamine solution, and a superior part of the membrane in contact with a zone that forms an air chamber into the closure.
20. The ketamine product of any one of items 18 to 19, wherein the twist-off closure comprises at least one layer of polypropylene.
21. The ketamine product of any one of items 18 to 20, wherein the twist-off closure comprises at least one layer of polyethylene.
22. The ketamine product of any one of items 11-21, wherein the port comprises at least one layer of block copolymer.
23. The ketamine product of any one of items 11-22, wherein the port comprises more than one layer of a block copolymer.
24. The ketamine product of any one of items 11-23, wherein the port comprises more than one layer of a polyolefin block copolymer.
25. The ketamine product of any one of items 11-24, wherein the infusion bag comprises a flexible multilayer film.
26. The ketamine product of any one of items 11-25, wherein the infusion bag comprises a flexible multilayer film comprising polyolefin, polyethylene, polypropylene, modified polyolefin-polyethylene polymers, styrene-polyolefin based polymers, block copolymers, or any combination thereof.
27. The ketamine product of any one of items 11-26, wherein the infusion bag comprises a flexible multilayer film comprising polyolefin and styrene-ethylene-butylene (SEB) block copolymer.
28. The ketamine product of any one of items 11-27, wherein the infusion bag comprises a flexible multilayer film comprising polypropylene styrene-block copolymer.
29. The ketamine product of any one of items 11-28, wherein the infusion bag comprises a flexible multilayer film comprising 2 to 5 layers, wherein at least one layer comprises polypropylene styrene-block copolymer.
30. The ketamine product of any one of items 11-29, wherein the infusion bag comprises a 3-layer film comprising polypropylene styrene-block copolymer.
31. The ketamine product of any one of items 11-30, wherein the infusion bag is contained within an overwrap.
32. The ketamine product of item 31, wherein the overwrap comprises polyester, aluminum, polypropylene, or a combination thereof.
33. The ketamine product of any one of items 31 to 32, wherein the overwrap comprises four layers comprising polyester, aluminum, polypropylene, and polyester.
34. The ketamine product of any preceding item, wherein the ketamine product has been autoclaved.
35. A ketamine product comprising an aqueous ketamine solution comprising about 0.5 to about 2.5 mg/mL ketamine, a tonicity adjusting agent, a pH adjusting agent, and water for injection, wherein the ketamine solution is preservative-free, and wherein the ketamine solution is contained in a terminally sterilized, ready-to-use infusion container.
36. The ketamine product of item 35, wherein the ketamine is at a concentration of about 1 to about 2 mg/mL.
37. The ketamine product of any preceding item, wherein the ketamine product has a shelf-life of more than three months when stored at a controlled room temperature.

38. The ketamine product of item 37, wherein the controlled room temperature is 15-30° C.
39. The ketamine product of any preceding item, wherein the ketamine or a pharmaceutically acceptable salt thereof is chemically stable for at least 24 months at 25° C.±2° C. with relative humidity (RH) at 40%±5%.
40. The ketamine product of any preceding item, wherein the average number of particles equal to or greater than 10 μm does not exceed 600 per container ketamine following storage of the ketamine product at room temperature for 24 months.
41. The ketamine product of any preceding item, wherein the average number of particles equal to or greater than 25 μm does not exceed 60 per container following storage of the ketamine product at room temperature for 24 months.
42. The ketamine product of any preceding item, wherein the total impurities in the aqueous ketamine solution is less than or equal to 1%.
43. The ketamine product of any preceding item, wherein the ketamine content of the aqueous ketamine solution after accelerated storage at 40° C.±2° C./<25% RH for 6 months is greater than 99%.
44. The ketamine product of any preceding item, wherein the bacterial endotoxin content is less than 0.4 EU/mg.
45. The ketamine product of any preceding item, wherein the ketamine content of the aqueous ketamine solution after long-term storage for 12 months at 25° C.±2° C./40% RH±5% RH is 99% or greater compared to the ketamine content before storage.
46. The ketamine product of any preceding item, containing about 250 mg ketamine hydrochloride.
47. The ketamine product of any preceding item, containing about 500 mg ketamine hydrochloride.
48. A method of preparing the ketamine product of any preceding item, comprising:
    i) adding ketamine or a pharmaceutically acceptable salt thereof to water;
    ii) adjusting the pH to about 3.5 to 5.5 using a pH adjusting agent;
    iii) filtering the solution of step (ii);
    iv) filling the solution of step (iii) into an infusion bag; and
    v) terminally sterilizing the infusion bag of step (iv).
49. The method of item 48 further comprising overwrapping the terminally sterilized infusion bag with an overwrap.
50. The method of any one of items 48-49, wherein the terminal sterilization comprises autoclaving the infusion bag.
51. The method of item 50, wherein said autoclaving is at a temperature ranging from 110 to 130° C. for a period of time ranging from 7 to 60 minutes.
52. The method of any one of items 50-51, wherein said autoclaving is at a temperature of 121° C. for a period of time ranging from 7 to 60 minutes.
53. The method of any one of items 50-52, wherein said autoclaving is at a temperature of 121° C. for about 15 minutes.
54. The method of any one of items 50-53, wherein the method comprises overwrapping the infusion bag of step (iv) prior to terminally sterilizing the infusion bag.
55. A method of treating a subject in need of analgesia, comprising administering the ketamine product of any one of items 1-47 to the subject as a continuous infusion.
56. The method of item 55, wherein the ketamine solution is administered by intravenous infusion.
57. The method of item 55 or item 56, wherein the subject is in need of anesthesia for a diagnostic or a surgical procedure.
58. The method of item 55 or item 56, wherein the subject is in need of anesthesia prior to administration of an anesthetic agent other than ketamine or a pharmaceutically acceptable salt thereof.
59. The method of item 55 or item 56, wherein the subject is in need of ketamine administration in addition to administration of an anesthetic agent other than ketamine or a pharmaceutically acceptable salt thereof.
60. A ketamine product comprising an aqueous ketamine solution comprising about 0.5 to about 2.5 mg/mL ketamine, a tonicity adjusting agent, a pH adjusting agent, and water for injection, wherein the ketamine solution is contained in an infusion bag comprising at least one port sealed with a closure, wherein the ketamine product has been aseptically filled, and wherein the ketamine product is ready-to-use (RTU).

EXAMPLES

The following examples are merely illustrative of the presently disclosed subject matter and they should not be considered as limiting the scope of the present disclosure in any way.

Example 1: Exemplary Formulations

In one embodiment, the ketamine product comprises the composition of Table 1.

TABLE 1

Ketamine Hydrochloride in Sodium Chloride Injection 1 mg/mL

| Active Substance(s) | Quantity per Unit (mg/mL) | Quantity per Unit (250 mL container) | Function | Reference Standard |
|---|---|---|---|---|
| Ketamine as Ketamine HCl | 1 mg/mL 1.15 mg/mL | 250 mg | API | USP |
| Excipient(s) | | | | |
| Sodium Chloride | 9 mg/mL | 2250 mg/mL | Tonicity agent | USP/NF |
| Water for Injection | q.s 1/mL | q.s 250 mL | Solvent | USP |

In another embodiment, the ketamine product may comprise the composition of Table 2.

TABLE 2

Ketamine Hydrochloride in Sodium Chloride Injection 2 mg/mL

| Active Substance(s) | Quantity per Unit (mg/mL) | Quantity per Unit (250 mL container) | Function | Reference Standard |
|---|---|---|---|---|
| Ketamine as Ketamine HCl | 2 mg/mL 2.3 mg/mL | 500 mg | API | USP |
| Excipient(s) | | | | |
| Sodium Chloride | 9 mg/mL | 2250 mg/mL | Tonicity agent | USP/NF |
| Water for Injection | q.s 1/mL | q.s 250 mL | Solvent | USP |

In another embodiment, the ketamine product may comprise the composition of Table 3.

TABLE 3

Ketamine in Sodium Chloride Injection 1 mg/mL

| Active Substance(s) | Quantity per Unit (mg/mL) | Quantity per Unit (250 mL container) | Function | Reference Standard |
|---|---|---|---|---|
| Ketamine (free base) | 1 mg/mL | 250 mg | API | USP |
| Excipient(s) | | | | |
| Sodium Chloride | 9 mg/mL | 2250 mg/mL | Tonicity agent | USP/NF |
| Water for Injection | q.s 1/mL | q.s 250 mL | Solvent | USP |

In another embodiment, the ketamine product may comprise the composition of Table 4.

TABLE 4

Ketamine in Sodium Chloride Injection 2 mg/mL

| Active Substance(s) | Quantity per Unit (mg/mL) | Quantity per Unit (250 mL container) | Function | Reference Standard |
|---|---|---|---|---|
| Ketamine (free base) | 2 mg/mL | 500 mg | API | USP |
| Excipient(s) | | | | |
| Sodium Chloride | 9 mg/mL | 2250 mg/mL | Tonicity agent | USP/NF |
| Water for Injection | q.s 1/mL | q.s 250 mL | Solvent | USP |

The inventors contemplate that additional ketamine products may be provided in different volumes with the same proportion of components as listed in Tables 1-4 above. Further, the inventors contemplate that other solvent systems may be substituted for the sodium chloride and water for injection. As one example, 5% dextrose in water for injection may be used in place of sodium chloride in water for injection in the formulations above. Further the inventors contemplate that any pharmaceutically acceptable salt of ketamine may be used in the formulations above, using the concentration of ketamine as the free base listed in Tables 3 and 4 above. The ketamine formulations above beneficially do not require an antimicrobial such as benzethonium chloride. The ketamine formulations above beneficially do not require any preservative. Nonetheless, the inventors contemplate that one or more excipients, such as a chelating or complexing agent or an antioxidant, may be added to the formulation without reducing the stability of the ready-to-use ketamine product described herein.

Example 2: Study of Stability Following Terminal Sterilization

Batches of the ketamine solution with the formulations described in Table 1 (1 mg/ml) and Table 2 (2 mg/ml) were manufactured to study the effect of terminal sterilization by autoclaving on product behavior. The primary packaging for each formulation included an infusion bag comprising a flexible multilayer film comprising a 3-layer polypropylene styrene-block copolymer based film (APP114S film manufactured by Polycine); a tube port comprising a multilayer polyolefin and styrene block copolymer tube material (APP107 manufactured by Polycine); and a twist off closure composed of low density polyethylene (LDPE) and polypropylene (PP). The closure comprised a membrane that created a barrier, wherein the inferior part of the membrane was in direct contact with the ketamine solution, while the superior part was in contact with a zone that forms an air chamber into the closure. Autoclaving of the primary packaging filled with the preservative-free ketamine formulations of Table 1 (1 mg/ml) and Table 2 (2 mg/ml), respectively, was conducted at a target temperature T=121° C.±1° C. and time at F0=15 according to USP <1222>, which is incorporated fully herein.

The objective of this study was to evaluate the quality of ketamine formulation seven days after the product is exposed to terminal sterilization processes at 121° C. at different F=0. Only slight, not significant, pH decrease was noted. There was no significant variation on assay (%) of ketamine from before to after sterilization.

pH decrease after sterilization was equal to 0.5 pH units which was in-line with results obtained on laboratory batches where decrease was equal to 0.4 pH units.

The results of Tables 5 show that the ketamine product of the invention can be terminally sterilized using autoclaving at a target temperature T=121° C.±1° C. and time at F0=15 according to USP <1222> without affecting the quality of ketamine formulation.

Example 3: Stability Studies

The terminally sterilized infusion bags, as described in Example 2, comprising a preservative-free aqueous ketamine solution with the formulation described in Table 1 (1 mg/ml) or Table 2 (2 mg/ml) were compared to a commercially available concentrated ketamine solution product in

TABLE 5

Assay and pH before vs after sterilization

| | Product | | | | | |
|---|---|---|---|---|---|---|
| | Ketamine Formulation 1 mg/ml | | | Ketamine Formulation 2 mg/ml | | |
| Batch | Batch 1 | Batch 2 | Batch 3 | Batch 4 | Batch 5 | Batch 6 |
| Average Assay pre-sterilization (% of Ketamine base) | 100.6 | 101.5 | 100.9 | 100.1 | 101.7 | 100.0 |
| Assay post-sterilization (FP) (% of labelled amount of Ketamine base) | 100.5 | 101.7 | 100.6 | 100.6 | 101.7 | 100.5 |
| Extractable volume (ml) | 251 | 252 | 251 | 252 | 251 | 252 |
| Assay post-sterilization (FP) (% of Ketamine base) | 100.1 | 100.9 | 100.2 | 99.8 | 101.3 | 99.7 |
| Assay % change post- VS pre-sterilization | −0.5 | −0.6 | −0.7 | −0.3 | −0.4 | −0.3 |
| pH pre-sterilization (end of filling) | 5.2 | 4.8 | 5.2 | 4.9 | 4.8 | 5.2 |
| pH post-sterilization (FP) | 4.6 | 4.5 | 4.6 | 4.6 | 4.4 | 4.7 |
| Change in pH (post VS pre-sterilization) | −0.6 | −0.3 | −0.6 | −0.3 | −0.4 | −0.5 |

For the ketamine product with the formulation described in Table 1 (1 mg/ml) the maximum pH decrease after sterilization was equal to 0.6 pH units which was in-line with results obtained on laboratory batches where decrease was equal to 0.5 pH units.

For the ketamine product of the disclosure with the formulation described in Table 2 (2 mg/ml) the maximum multi-dose glass vials containing the preservative benzethonium chloride. The commercially available concentrated products were diluted with 0.9% sodium chloride in a glass volumetric flask to achieve a concentration of 1 mg/mL or 2 mg/mL of Ketamine. The results for the 1 mg/ml and 2 mg/ml products are shown in Tables 6 and 7, respectively.

TABLE 6

Accelerated Condition 40 ± 2° C./<25% RH - 6 months

| | Batch | | | | |
|---|---|---|---|---|---|
| Test | Commercial Product Batch 1 (1 mg/mL) | Commercial Product Batch 2 (1 mg/mL) | Ketamine Product of the Disclosure Batch 1 (1 mg/mL) | Ketamine Product of the Disclosure Batch 2 (1 mg/mL) | Ketamine Product of the Disclosure Batch 3 (1 mg/mL) |
| Appearance (Clear, colorless to slightly yellow, free from visible particle) | Comply | Comply | Comply | Comply | Comply |
| Assay (% labeled amount as ketamine) | 101.2 | 101.4 | 100.5 | 101.7 | 100.6 |

TABLE 6-continued

Accelerated Condition 40 ± 2° C./<25% RH - 6 months

| Test | Commercial Product Batch 1 (1 mg/mL) | Commercial Product Batch 2 (1 mg/mL) | Ketamine Product of the Disclosure Batch 1 (1 mg/mL) | Ketamine Product of the Disclosure Batch 2 (1 mg/mL) | Ketamine Product of the Disclosure Batch 3 (1 mg/mL) |
|---|---|---|---|---|---|
| Impurities: | | | | | |
| Specified identified impurity-Impurity A (%) | <0.05 | <0.05 | <0.05 | <0.05 | <0.05 |
| Specified identified impurity-Impurity B (%) | <0.05 | <0.05 | <0.05 | <0.05 | <0.05 |
| Specified identified impurity-Impurity C (%) | <0.05 | <0.05 | <0.05 | <0.05 | <0.05 |
| Unspecified unidentified impurity (%) | <0.05 | <0.05 | <0.05 | <0.05 | <0.05 |
| Total impurity (%) | <0.05 | <0.05 | <0.05 | <0.05 | <0.05 |
| pH (pH Units) | 5.0 | 5.0 | 4.7 | 4.5 | 4.8 |
| Osmolality (mOsmol/kg) | 291 | 286 | 296 | 298 | 296 |

TABLE 7

Accelerated Condition 40 ± 2° C./<25% RH - 6 months

| Test | Commercial Product Batch 1 (2 mg/mL) | Commercial Product Batch 2 (2 mg/mL) | Ketamine Product of the Disclosure Batch 1 (2 mg/mL) | Ketamine Product of the Disclosure Batch 2 (2 mg/mL) | Ketamine Product of the Disclosure Batch 3 (2 mg/mL) |
|---|---|---|---|---|---|
| Appearance (Clear, colorless to slightly yellow, free from visible particle) | Comply | Comply | Comply | Comply | Comply |
| Assay (% labeled amount as ketamine) | 100.2 | 100.7 | 100.4 | 101.5 | 100.4 |
| Impurities: | | | | | |
| Specified identified impurity-Impurity A (%) | <0.05 | <0.05 | <0.05 | <0.05 | <0.05 |
| Specified identified impurity-Impurity B (%) | <0.05 | <0.05 | <0.05 | <0.05 | <0.05 |
| Specified identified impurity-Impurity C (%) | <0.05 | <0.05 | <0.05 | <0.05 | <0.05 |
| Unspecified unidentified impurity (%) | <0.05 | <0.05 | <0.05 | <0.05 | <0.05 |
| Total impurity (%) | <0.05 | <0.05 | <0.05 | <0.05 | <0.05 |
| pH (pH Units) | 4.9 | 4.9 | 4.6 | 4.5 | 4.6 |
| Osmolality (mOsmol/kg) | 297 | 288 | 304 | 305 | 304 |

TABLE 8

Long term Condition 25 ± 2° C./40 ± 5% RH - 12 months

| Test | Commercial Product Batch 1 (1 mg/mL) | Commercial Product Batch 2 (1 mg/mL) | Ketamine Product of the Disclosure Batch 1 (1 mg/mL) | Ketamine Product of the Disclosure Batch 2 (1 mg/mL) | Ketamine Product of the Disclosure Batch 3 (1 mg/mL) |
|---|---|---|---|---|---|
| Appearance (Clear, colorless to slightly yellow, free from visible particle) | Comply | Comply | Comply | Comply | Comply |
| Assay (% labeled amount as ketamine) | 100.9 | 102.1 | 100.5 | 101.9 | 100.7 |
| Impurities: | | | | | |
| Specified identified impurity- Impurity A (%) | <0.05 | <0.05 | <0.05 | 0.05 | 0.06 |
| Specified identified impurity- Impurity B (%) | <0.05 | <0.05 | <0.05 | <0.05 | <0.05 |
| Specified identified impurity- Impurity C (%) | <0.05 | <0.05 | <0.05 | <0.05 | <0.05 |
| Unspecified unidentified impurity (%) | <0.05 | <0.05 | <0.05 | <0.05 | <0.05 |
| Total impurity (%) | <0.05 | <0.05 | <0.05 | 0.05 | 0.06 |
| pH (pH Units) | 5.1 | 5.0 | 4.8 | 4.5 | 4.8 |
| Osmolality (mOsmol/kg) | 287 | 290 | 293 | 294 | 295 |

TABLE 9

Long term Condition 25 ± 2° C./40 ± 5% RH - 12 months

| Batch Test | Commercial Product Batch 1 (2 mg/mL) | Commercial Product Batch 2 (2 mg/mL) | Ketamine Product of the Disclosure Batch 1 (2 mg/mL) | Ketamine Product of the Disclosure Batch 2 (2 mg/mL) | Ketamine Product of the Disclosure Batch 3 (2 mg/mL) |
|---|---|---|---|---|---|
| Appearance (Clear, colorless to slightly yellow, free from visible particle) | Comply | Comply | Comply | Comply | Comply |
| Assay (% labeled amount as ketamine) | 100.3 | 102.3 | 100.5 | 101.7 | 100.6 |
| Impurities: | | | | | |
| Specified identified impurity- Impurity A (%) | <0.05 | <0.05 | <0.05 | <0.05 | <0.05 |
| Specified identified impurity- Impurity B (%) | <0.05 | <0.05 | <0.05 | <0.05 | <0.05 |
| Specified identified impurity- Impurity C (%) | <0.05 | <0.05 | <0.05 | <0.05 | <0.05 |

TABLE 9-continued

Long term Condition 25 ± 2° C./40 ± 5% RH - 12 months

| Batch<br>Test<br>Appearance | Commercial<br>Product<br>Batch 1<br>(2 mg/mL)<br>Comply | Commercial<br>Product<br>Batch 2<br>(2 mg/mL)<br>Comply | Ketamine<br>Product of the<br>Disclosure<br>Batch 1<br>(2 mg/mL)<br>Comply | Ketamine<br>Product of the<br>Disclosure<br>Batch 2<br>(2 mg/mL)<br>Comply | Ketamine<br>Product of the<br>Disclosure<br>Batch 3<br>(2 mg/mL)<br>Comply |
|---|---|---|---|---|---|
| Unspecified unidentified impurity (%) | <0.05 | <0.05 | <0.05 | <0.05 | <0.05 |
| Total impurity (%) | <0.05 | <0.05 | <0.05 | <0.05 | <0.05 |
| pH (pH Units) | 4.9 | 4.9 | 4.6 | 4.5 | 4.8 |
| Osmolality (mOsmol/kg) | 287 | 299 | 301 | 303 | 303 |

After 6 months of stability testing at 40° C., there was no observed variation in the pH and in the color of the ketamine products of the disclosure contained in ready-to-use, terminally sterilized, infusion bags. After 6 months at 40° C. there was no observed reduction in Ketamine Hydrochloride Assay compared to T=0 sterilized. The total impurities of the preservative-free ketamine formulations of the disclosure, packaged in ready-to-use, terminally sterilized, infusion bags were comparable with the results obtained at T=0.

The results of Tables 6-9 surprisingly show that the terminally sterilized ketamine products described herein, formulated without any antimicrobial, stabilizer or preservative, are at least as stable as the commercial formulation with benzethonium chloride under accelerated conditions and long-term storage. While the average pH of ketamine solution in infusion bags seen in the experiment was 4.5-4.8 pH units and the average pH of the commercially available product when diluted for use was 4.9-5.2, the ketamine solution in infusion bags remained stable. Additionally, osmolality of ketamine solution in infusion bags seen in the experiment was comparable to the commercially available product, and both were inside the physiological range (according to the USP <785>, which is incorporated fully herein, the osmolality of blood ranges between 285 and 310 mOsmol/kg) and therefore comparable in the context of this evaluation. No significant change was noted during the stability studies and no degradation was detected despite of a lack of any antimicrobial, stabilizer or preservative in the ketamine products of the present disclosure.

Example 4: Stress Studies

The ketamine product of the disclosure was analyzed to evaluate critical product characteristics/parameters under stressed conditions. Stress testing was intended to identify the likely degradation products, which further helped in determination of the intrinsic stability of the molecule and establishing degradation pathways, and to validate the stability indicating procedures used.

An oxidative stress study was conducted in accordance with the procedure set out in FIG. 1. The results for the 1 mg/mL and 2 mg/mL formulations (as described in Tables 1 and 2, respectively) treated with hydrogen peroxide in a ratio of 1:1 are shown in Tables 10 and 11, respectively, where "Δ" refers to the difference between the test batch and the blank sample. The "blank sample" refers to the formulation of Table 1 (1 mg/ml) or Table 2 (2 mg/ml) without addition of hydrogen peroxide, while the "test batch" refers to the formulation with addition of hydrogen peroxide in a 1:1 ratio. The oxidative degradation 1:1 reported data was collected 72 hours after addition of the hydrogen peroxide.

TABLE 10

Oxidative degradation results of ketamine solution
250 mg/250 mL (1 mg/ml) in ratio 1:1 with $H_2O_2$

| Test | Specifications | Unit | Blank sample | Test Batch (1 mg/ml) | Δ |
|---|---|---|---|---|---|
| Completeness of Solution | Free from visible particles | — | Free from visible particles | Free from visible particles | — |
| Appearance of solution - Color | Colorless to slightly yellow | — | Complies | Complies | — |
| Appearance of solution - Clarity | Clear | — | Clear | Clear | — |
| pH | 3.5-5.5 | pH Units | 4.74 | 4.58 | −0.16 |
| Osmolality | 270-330 | mOsmol/Kg | 296 | 295 | −1 |
| Assay | 95.0-105.0 | % | 100.0 | 99.6 | −0.4 |
| Impurities: | | | | | |
| Ketamine related compound A | NMT 0.20 | % | <0.05 | <0.05 | 0 |

TABLE 10-continued

Oxidative degradation results of ketamine solution
250 mg/250 mL (1 mg/ml) in ratio 1:1 with $H_2O_2$

| Test | Specifications | Unit | Blank sample | Test Batch (1 mg/ml) | Δ |
|---|---|---|---|---|---|
| Unspecified unidentified impurity | NMT 0.20 | % | <0.05 | <0.05 | 0 |
| Total impurities | NMT 1.0 | % | <0.05 | <0.05 | 0 |
| Particulate matter: | | | | | |
| ≥10 micron | NMT 23 | No part/mL | 0 | 0 | 0 |
| ≥25 micron | NMT 3 | | 0 | 0 | 0 |

TABLE 11

Oxidative degradation results of ketamine solution
500 mg/250 mL (2 mg/ml) in ratio 1:1 with $H_2O_2$

| Test | Specifications | Unit | Blank sample | Test Batch (2 mg/ml) | Δ |
|---|---|---|---|---|---|
| Completeness of Solution | Free from visible particles | — | Free from visible particles | Free from visible particles | — |
| Appearance of solution - Color | Colorless to slightly yellow | — | Complies | Complies | — |
| Appearance of solution - Clarity | Clear | — | Clear | Clear | — |
| pH | 3.5-5.5 | pH Units | 4.60 | 4.56 | −0.04 |
| Osmolality | 270-330 | mOsmol/Kg | 299 | 308 | +9 |
| Assay | 95.0-105.0 | % | 99.7 | 99.6 | −0.1 |
| Impurities: | | | | | |
| Ketamine related compound A | NMT 0.20 | % | <0.05 | <0.05 | 0 |
| Unspecified unidentified impurity | NMT 0.20 | % | <0.05 | <0.05 | 0 |
| Total impurities | NMT 1.0 | % | <0.05 | <0.05 | 0 |
| Particulate matter: | | | | | |
| ≥10 micron | NMT 23 | No part/mL | 0 | 0 | 0 |
| ≥25 micron | NMT 3 | | 0 | 0 | 0 |

The results shown in Tables 10-11 demonstrate that the ketamine product of the invention is stable, as no significant degradation of the ketamine solution was observed after 72 hours after the ketamine solution was treated with hydrogen peroxide in stoichiometric ratio 1:1.

The results of the oxidative stress for the 1 mg/mL and 2 mg/mL formulations (as described in Tables 1 and 2, respectively) treated with hydrogen peroxide in a ratio of 1:10 are shown in Tables 12 and 13, respectively, where "Δ" refers to the difference between the blank sample and Batch 1. The "blank sample" refers to the formulation of Table 1 (1 mg/ml) or Table 2 (2 mg/ml) without addition of hydrogen peroxide, while the "test batch" refers to the formulation with addition of hydrogen peroxide in a 1:10 ratio. The reported data was collected 48 hours after addition of the hydrogen peroxide.

TABLE 12

Oxidative degradation results of ketamine solution
250 mg/250 mL (1 mg/ml) in ratio 1:10 with $H_2O_2$

| Test | Specifications | Unit | Blank sample | Test Batch (1 mg/ml) | Δ |
|---|---|---|---|---|---|
| Assay | 95.0-105.0 | % | 100.2 | 99.2 | −1.0 |
| Impurities: | | | | | |
| Ketamine related compound A | NMT 0.20 | % | <0.05 | <0.05 | 0 |
| Unspecified unidentified impurity RT 5.3 | NMT 0.20 | % | <0.05 | 0.13 | +0.13 |
| Unspecified unidentified impurity RT 9.0 | NMT 0.20 | % | <0.05 | 0.14 | +0.14 |
| Total impurities | NMT 1.0 | % | <0.05 | 0.27 | +0.27 |

TABLE 13

Oxidative degradation results of ketamine solution 500 mg/250 mL in ratio 1:10 with $H_2O_2$

| Test | Specifications | Unit | Blank sample | Test Batch (2 mg/ml) | Δ |
|---|---|---|---|---|---|
| Assay | 95.0-105.0 | % | 100.1 | 99.5 | −0.6 |
| Impurities: | | | | | |
| Ketamine related compound A | NMT 0.20 | % | <0.05 | <0.05 | 0 |
| Unspecified unidentified impurity RT 5.3 | NMT 0.20 | % | <0.05 | 0.08 | 0.08 |
| Unspecified unidentified impurity RT 9.0 | NMT 0.20 | % | <0.05 | 0.08 | 0.08 |
| Total impurities | NMT 1.0 | % | <0.05 | 0.16 | 0.16 |

The results shown in Tables 12-13 demonstrate that there was a slight increase in impurities in the ketamine solution after 48 hours after the ketamine solution was treated with hydrogen peroxide in ratio 1:10.

Figure 2:
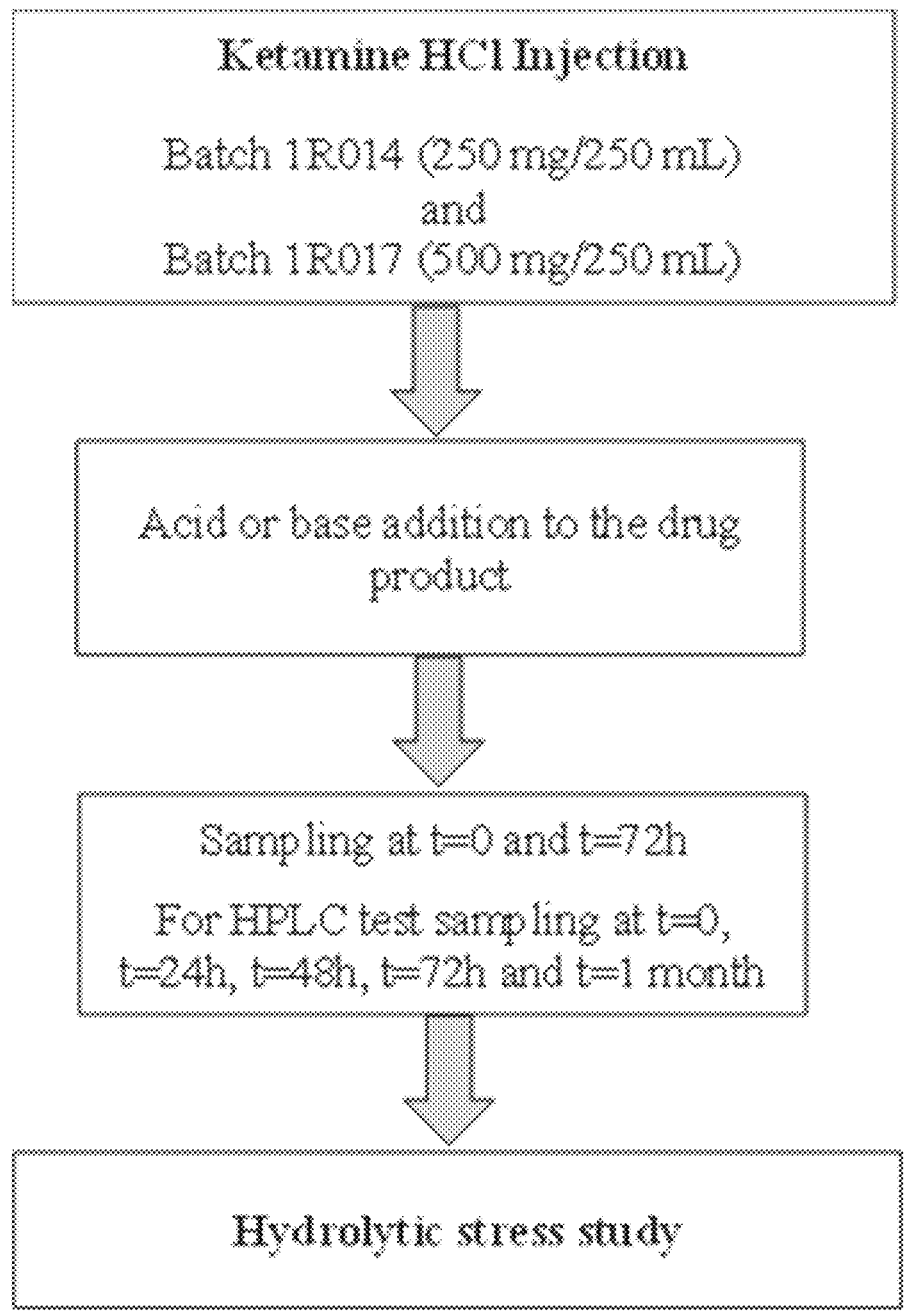
FIG. 2 shows the steps and specifications of the acid alkaline stress study conducted on the ready to use sterile infusion bag comprising a preservative-free aqueous ketamine solution of the disclosure ("ketamine HCL injection"). An acid or base was added to two batches of ketamine HCL injection (1R014 and 1R017) at two different concentrations (1 mg/mL and 2 mg/mL respectively). HPLC tests were performed to determine the effects of hydrolytic stress on the ketamine HCL injection product.
Figure 3:
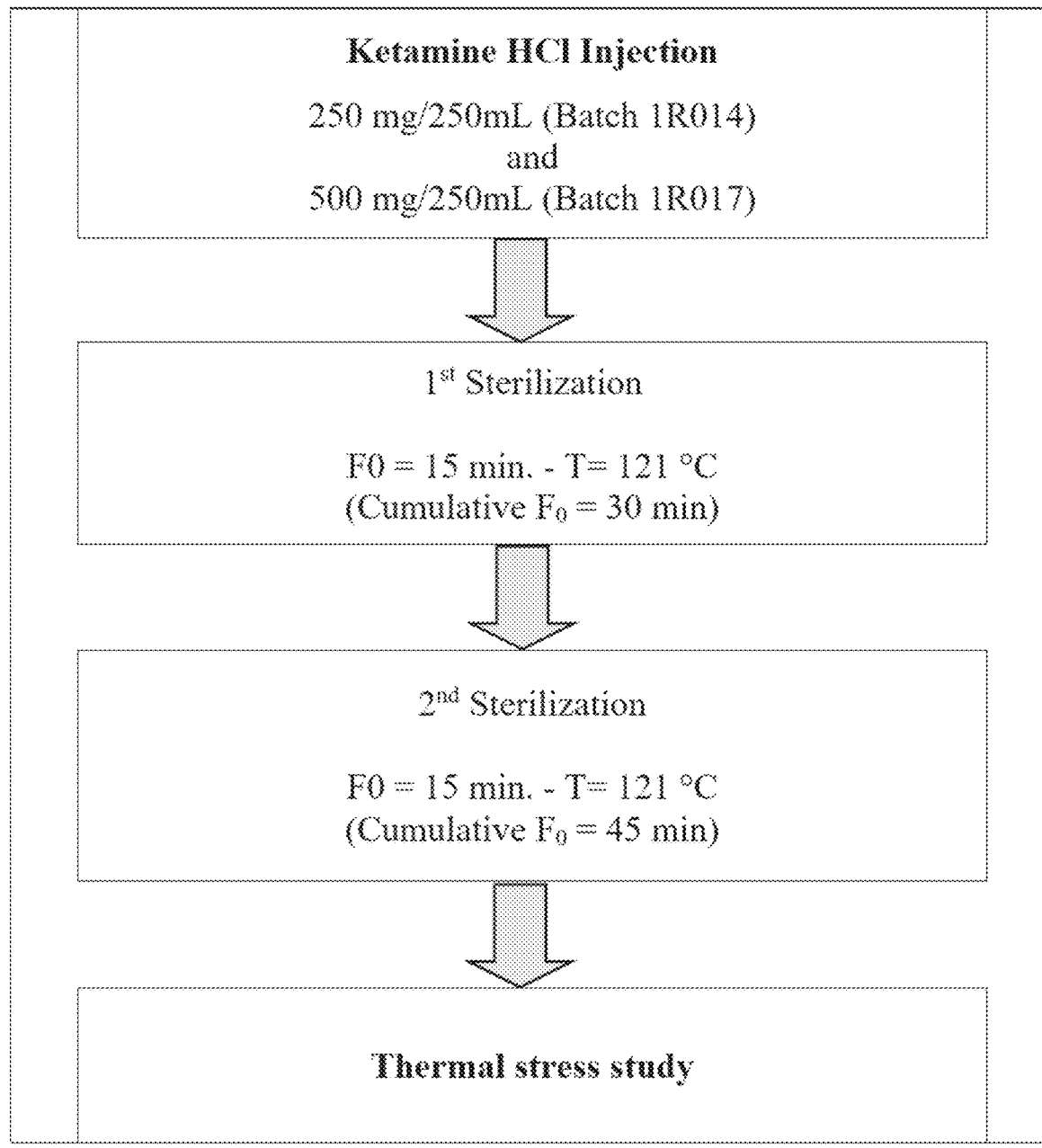
FIG. 3 shows the steps and specifications of the thermal stress study conducted on the ready to use terminally sterilized infusion bag comprising a preservative-free aqueous ketamine solution of the disclosure ("ketamine HCL injection"). Two batches of ketamine HCL injection (1R014 and 1R017) at two different concentrations (1 mg/mL and 2 mg/mL respectively) were subjected to two autoclave cycles. Tests were performed to determine the effects of thermal stress on the ketamine HCL injection product, the results of which are shown in tables 22 and 23.

An acid/alkaline study was conducted in accordance with the procedure set out in FIG. 2. These results demonstrate that the ketamine product of the invention is stable, as no significant degradation of the ketamine solution was observed through one month of observation (t=1 M) compared to the blank sample. The "blank sample" refers to the formulation of Table 1 (1 mg/ml) or Table 2 (2 mg/ml) at pH 4.7, while the "test batch" refers to the formulation at varying test pH.

TABLE 14

Degradation results of ketamine solution 250 mg/250 mL at pH 2.5

| Test | Specifications | Unit | Blank sample | t = 24 h | t = 48 h | t = 72 h | t = 1M |
|---|---|---|---|---|---|---|---|
| Completeness of Solution | Free from visible particles | — | Free from visible particles | — | — | Free from visible particles | — |
| Appearance of solution - Color | Colorless to slightly yellow | — | Complies | — | — | Complies | — |
| Appearance of solution - Clarity | Clear | — | Clear | — | — | Clear | — |
| pH | NA* | pH Units | 4.7 | — | — | 2.5 | — |
| Osmolality | 270-330 | mOsmol/Kg | 293 | — | — | 300 | — |
| Assay | 95.0-105.0 | % | 100.3 | 100.4 | 100.0 | 100.2 | 100.4 |
| Impurities | | | | | | | |
| Ketamine related compound A | NMT 0.20 | % | <0.05 | <0.05 | <0.05 | <0.05 | <0.05 |
| Unspecified unidentified impurity | NMT 0.20 | % | <0.05 | <0.05 | <0.05 | <0.05 | <0.05 |
| Total impurities | NMT 1.0 | % | <0.05 | <0.05 | <0.05 | <0.05 | <0.05 |
| Particulate matter: | | | | | | | |
| ≥10 micron | NMT 23 | No part/mL | 0 | — | — | 0 | 0 |
| ≥25 micron | NMT 3 | | 0 | | | 0 | 0 |

TABLE 15

Degradation results of ketamine solution 250 mg/250 mL at pH 3.5

| Test | Specifications | Unit | Blank sample | t = 24 h | t = 48 h | t = 72 h | t = 1M |
|---|---|---|---|---|---|---|---|
| Completeness of Solution | Free from visible particles | — | Free from visible particles | — | — | Free from visible particles | — |
| Appearance of solution - Color | Colorless to slightly yellow | — | Complies | — | — | Complies | — |
| Appearance of solution - Clarity | Clear | — | Clear | — | — | Clear | — |

TABLE 15-continued

Degradation results of ketamine solution 250 mg/250 mL at pH 3.5

| Test | Specifications | Unit | Blank sample | t = 24 h | t = 48 h | t = 72 h | t = 1M |
|---|---|---|---|---|---|---|---|
| pH | NA* | pH Units | 4.7 | — | — | 3.5 | — |
| Osmolality | 270-330 | mOsmol/Kg | 293 | — | — | 294 | — |
| Assay | 95.0-105.0 | % | 100.2 | 100.1 | 100.2 | 100.1 | 100.2 |
| Impurities | | | | | | | |
| Ketamine related compound A | NMT 0.20 | % | <0.05 | <0.05 | <0.05 | <0.05 | <0.05 |
| Unspecified unidentified impurity | NMT 0.20 | % | <0.05 | <0.05 | <0.05 | <0.05 | <0.05 |
| Total impurities | NMT 1.0 | % | <0.05 | <0.05 | <0.05 | <0.05 | <0.05 |
| Particulate matter: | | | | | | | |
| ≥10 micron | NMT 23 | No part/mL | 0 | — | — | 0 | 0 |
| ≥25 micron | NMT 3 | | 0 | | | 0 | 0 |

TABLE 16

Degradation results of ketamine solution 250 mg/250 mL at pH 5.5

| Test | Specifications | Unit | Blank sample | t = 24 h | t = 48 h | t = 72 h | t = 1M |
|---|---|---|---|---|---|---|---|
| Completeness of Solution | Free from visible particles | — | Free from visible particles | — | — | Free from visible particles | — |
| Appearance of solution - Color | Colorless to slightly yellow | — | Complies | — | — | Complies | — |
| Appearance of solution - Clarity | Clear | — | Clear | — | — | Clear | — |
| pH | NA* | pH Units | 4.7 | — | — | 3.5 | — |
| Osmolality | 270-330 | mOsmol/Kg | 293 | — | — | 294 | — |
| Assay | 95.0-105.0 | % | 100.2 | 100.1 | 100.2 | 100.1 | 100.2 |
| Impurities | | | | | | | |
| Ketamine related compound A | NMT 0.20 | % | <0.05 | <0.05 | <0.05 | <0.05 | <0.05 |
| Unspecified unidentified impurity | NMT 0.20 | % | <0.05 | <0.05 | <0.05 | <0.05 | <0.05 |
| Total impurities | NMT 1.0 | % | <0.05 | <0.05 | <0.05 | <0.05 | <0.05 |
| Particulate matter: | | | | | | | |
| ≥10 micron | NMT 23 | No part/mL | 0 | — | — | 0 | 0 |
| ≥25 micron | NMT 3 | | 0 | | | 0 | 0 |

TABLE 17

Degradation results of ketamine solution 250 mg/250 mL at pH 6.5

| Test | Specifications | Unit | Blank sample | t = 24 h | t = 48 h | t = 72 h | t = 1M |
|---|---|---|---|---|---|---|---|
| Completeness of Solution | Free from visible particles | — | Free from visible particles | — | — | Free from visible particles | — |
| Appearance of solution - Color | Colorless to slightly yellow | — | Complies | — | — | Complies | — |
| Appearance of solution - Clarity | Clear | — | Clear | — | — | Clear | — |

TABLE 17-continued

Degradation results of ketamine solution 250 mg/250 mL at pH 6.5

| Test | Specifications | Unit | Blank sample | t = 24 h | t = 48 h | t = 72 h | t = 1M |
|---|---|---|---|---|---|---|---|
| pH | NA* | pH Units | 4.7 | — | — | 6.5 | — |
| Osmolality | 270-330 | mOsmol/Kg | 293 | — | — | 295 | — |
| Assay | 95.0-105.0 | % | 100.23 | 100.3 | 100.3 | 100.4 | 100.1 |
| Impurities | | | | | | | |
| Ketamine related compound A | NMT 0.20 | % | <0.05 | <0.05 | <0.05 | <0.05 | <0.05 |
| Unspecified unidentified impurity | NMT 0.20 | % | <0.05 | <0.05 | <0.05 | <0.05 | <0.05 |
| Total impurities | NMT 1.0 | % | <0.05 | <0.05 | <0.05 | <0.05 | <0.05 |
| Particulate matter: | | | | | | | |
| ≥10 micron | NMT 23 | No part/mL | 0 | — | — | 0 | 0 |
| ≥25 micron | NMT 3 | | 0 | | | 0 | 0 |

TABLE 18

Degradation results of ketamine solution 500 mg/250 mL at pH 2.5

| Test | Specifications | Unit | Blank sample | t = 24 h | t = 48 h | t = 72 h | t = 1M |
|---|---|---|---|---|---|---|---|
| Completeness of Solution | Free from visible particles | — | Free from visible particles | — | — | Free from visible particles | — |
| Appearance of solution - Color | Colorless to slightly yellow | — | Complies | — | — | Complies | — |
| Appearance of solution - Clarity | Clear | — | Clear | — | — | Clear | — |
| pH | 3.5-5.5 | pH Units | 4.63 | — | — | 2.48 | — |
| Osmolality | 270-330 | mOsmol/Kg | 302 | — | — | 309 | — |
| Assay | 95.0-105.0 | % | 100.1 | 100.7 | 100.3 | 100.2 | 100.5 |
| Impurities | | | | | | | |
| Ketamine related compound A | NMT 0.20 | % | <0.05 | <0.05 | <0.05 | <0.05 | <0.05 |
| Unspecified unidentified impurity | NMT 0.20 | % | <0.05 | <0.05 | <0.05 | <0.05 | <0.05 |
| Total impurities | NMT 1.0 | % | <0.05 | <0.05 | <0.05 | <0.05 | <0.05 |
| Particulate matter: | | | | | | | |
| ≥10 micron | NMT 23 | No part/mL | 0 | — | — | 0 | 0 |
| ≥25 micron | NMT 3 | | 0 | | | 0 | 0 |

TABLE 19

Degradation results of ketamine solution 500 mg/250 mL at pH 3.5

| Test | Specifications | Unit | Blank sample | t = 24 h | t = 48 h | t = 72 h | t = 1M |
|---|---|---|---|---|---|---|---|
| Completeness of Solution | Free from visible particles | — | Free from visible particles | — | — | Free from visible particles | — |
| Appearance of solution - Color | Colorless to slightly yellow | — | Complies | — | — | Complies | — |

TABLE 19-continued

Degradation results of ketamine solution 500 mg/250 mL at pH 3.5

| Test | Specifications | Unit | Blank sample | t = 24 h | t = 48 h | t = 72 h | t = 1M |
|---|---|---|---|---|---|---|---|
| Appearance of solution - Clarity | Clear | — | Clear | — | — | Clear | — |
| pH | 3.5-5.5 | pH Units | 4.63 | — | — | 3.51 | — |
| Osmolality | 270-330 | mOsmol/Kg | 302 | — | — | 305 | — |
| Assay | 95.0-105.0 | % | 100.1 | 100.4 | 100.1 | 100.0 | 100.1 |
| Impurities | | | | | | | |
| Ketamine related compound A | NMT 0.20 | % | <0.05 | <0.05 | <0.05 | <0.05 | <0.05 |
| Unspecified unidentified impurity | NMT 0.20 | % | <0.05 | <0.05 | <0.05 | <0.05 | <0.05 |
| Total impurities | NMT 1.0 | % | <0.05 | <0.05 | <0.05 | <0.05 | <0.05 |
| Particulate matter: | | | | | | | |
| ≥10 micron | NMT 23 | No part/mL | 0 | — | — | 0 | 1 |
| ≥25 micron | NMT 3 | | 0 | — | — | 0 | 0 |

TABLE 20

Degradation results of ketamine solution 500 mg/250 mL at pH 5.5

| Test | Specifications | Unit | Blank sample | t = 24 h | t = 48 h | t = 72 h | t = 1M |
|---|---|---|---|---|---|---|---|
| Completeness of Solution | Free from visible particles | — | Free from visible particles | — | — | Free from visible particles | — |
| Appearance of solution - Color | Colorless to slightly yellow | — | Complies | — | — | Complies | — |
| Appearance of solution - Clarity | Clear | — | Clear | — | — | Clear | — |
| pH | 3.5-5.5 | pH Units | 4.63 | — | — | 5.51 | — |
| Osmolality | 270-330 | mOsmol/Kg | 302 | — | — | 303 | — |
| Assay | 95.0-105.0 | % | 100.1 | 100.2 | 100.2 | 100.2 | 100.1 |
| Impurities | | | | | | | |
| Ketamine related compound A | NMT 0.20 | % | <0.05 | <0.05 | <0.05 | <0.05 | <0.05 |
| Unspecified unidentified impurity | NMT 0.20 | % | <0.05 | <0.05 | <0.05 | <0.05 | <0.05 |
| Total impurities | NMT 1.0 | % | <0.05 | <0.05 | <0.05 | <0.05 | <0.05 |
| Particulate matter: | | | | | | | |
| ≥10 micron | NMT 23 | No part/mL | 0 | — | — | 0 | 0 |
| ≥25 micron | NMT 3 | | 0 | — | — | 0 | 0 |

TABLE 21

Degradation results of ketamine solution 500 mg/250 mL at pH 6.5

| Test | Specifications | Unit | Blank sample | t = 24 h | t = 48 h | t = 72 h | t = 1M |
|---|---|---|---|---|---|---|---|
| Completeness of Solution | Free from visible particles | — | Free from visible particles | — | — | Free from visible particles | — |
| Appearance of solution - Color | Colorless to slightly yellow | — | Complies | — | — | Complies | — |
| Appearance of solution - Clarity | Clear | — | Clear | — | — | Clear | — |
| pH | 3.5-5.5 | pH Units | 4.63 | — | — | 6.50 | — |
| Osmolality | 270-330 | mOsmol/Kg | 302 | — | — | 304 | — |
| Assay | 95.0-105.0 | % | 100.1 | 100.0 | 100.2 | 100.1 | 100.2 |
| Impurities | | | | | | | |
| Ketamine related compound A | NMT 0.20 | % | <0.05 | <0.05 | <0.05 | <0.05 | <0.05 |
| Unspecified unidentified impurity | NMT 0.20 | % | <0.05 | <0.05 | <0.05 | <0.05 | <0.05 |
| Total impurities | NMT 1.0 | % | <0.05 | <0.05 | <0.05 | <0.05 | <0.05 |
| Particulate matter: | | | | | | | |
| ≥10 micron | NMT 23 | No part/mL | 0 | — | — | 0 | 0 |
| ≥25 micron | NMT 3 | | 0 | | | 0 | 0 |

A heat degradation study was performed on the ketamine solution in infusion bags in accordance to the procedure set out in FIG. 2. The primary packaging used was the same infusion bags described in Example 2. No significant degradation of the ketamine solution in primary packaging was observed after two terminal sterilization cycles. The pH dropped slightly after each sterilization but it remained within the specification limits. These results demonstrate that the ketamine product of the invention is stable after two sterilization cycles conducted at 121° C. for 15 minutes each, as no significant change is noted in assay or impurity profile.

TABLE 22

Thermal stress results of Ketamine HCl Injection 250 mg/250 mL

| Test | Specifications | Unit | Blank sample | Sterilization F015 | Double sterilization F015 | Δ |
|---|---|---|---|---|---|---|
| Completeness of Solution | Free from visible particles | — | Free from visible particles | Free from visible particles | Free from visible particles | — |
| Appearance of solution - Color | Colorless to slightly yellow | — | Complies | Complies | Complies | — |
| Appearance of solution - Clarity | Clear | — | Clear | Clear | Clear | — |
| pH | 3.5-5.5 | pH Units | 4.7 | 4.5 | 4.3 | −0.4 |
| Osmolality | 270-330 | mOsmol/Kg | 296 | 292 | 294 | −2 |
| Assay | 95.0-105.0 | % | 100.0 | 99.5 | 98.9 | −1.2 |
| Impurities | | | | | | |
| Ketamine related compound A | NMT 0.20 | % | <0.05 | <0.05 | <0.05 | 0 |
| Unspecified unidentified impurity | NMT 0.20 | % | <0.05 | <0.05 | <0.05 | 0 |
| Total impurities | NMT 1.0 | % | <0.05 | <0.05 | <0.05 | 0 |
| Particulate matter: | | | | | | |
| ≥10 micron | NMT 23 | No part/mL | 0 | 0 | 1 | +1 |
| ≥25 micron | NMT 3 | | 0 | 0 | 0 | 0 |

TABLE 23

Thermal stress results of Ketamine HCl Injection 500 mg/250 mL

| Test | Specifications | Unit | Blank sample | Sterilization F015 | Double sterilization F015 | Δ |
|---|---|---|---|---|---|---|
| Completeness of Solution | Free from visible particles | — | Free from visible particles | Free from visible particles | Free from visible particles | — |
| Appearance of solution - Color | Colorless to slightly yellow | — | Complies | Complies | Complies | — |
| Appearance of solution - Clarity | Clear | — | Clear | Clear | Clear | — |
| pH | 3.5-5.5 | pH Units | 4.6 | 4.3 | 4.1 | −0.5 |
| Osmolality | 270-330 | mOsmol/Kg | 299 | 303 | 300 | +1 |
| Assay | 95.0-105.0 | % | 99.7 | 99.4 | 99.0 | −0.7 |
| Impurities | | | | | | |
| Ketamine related compound A | NMT 0.20 | % | <0.05 | <0.05 | <0.05 | 0 |
| Unspecified unidentified impurity | NMT 0.20 | % | <0.05 | <0.05 | <0.05 | 0 |
| Total impurities | NMT 1.0 | % | <0.05 | <0.05 | <0.05 | 0 |
| Particulate matter: | | | | | | |
| ≥10 micron | NMT 23 | No part/mL | 0 | 0 | 1 | +1 |
| ≥25 micron | NMT 3 | | 0 | 0 | 0 | 0 |

Example 5: Manufacturing Process Development

The ketamine product of the disclosure is an aqueous solution and is terminally sterilized. The manufacturing process involved dissolution of ketamine HCl in water for injection and addition of sodium chloride to adjust for tonicity in accordance to the procedure set out in FIG. 4.

Figure 5:
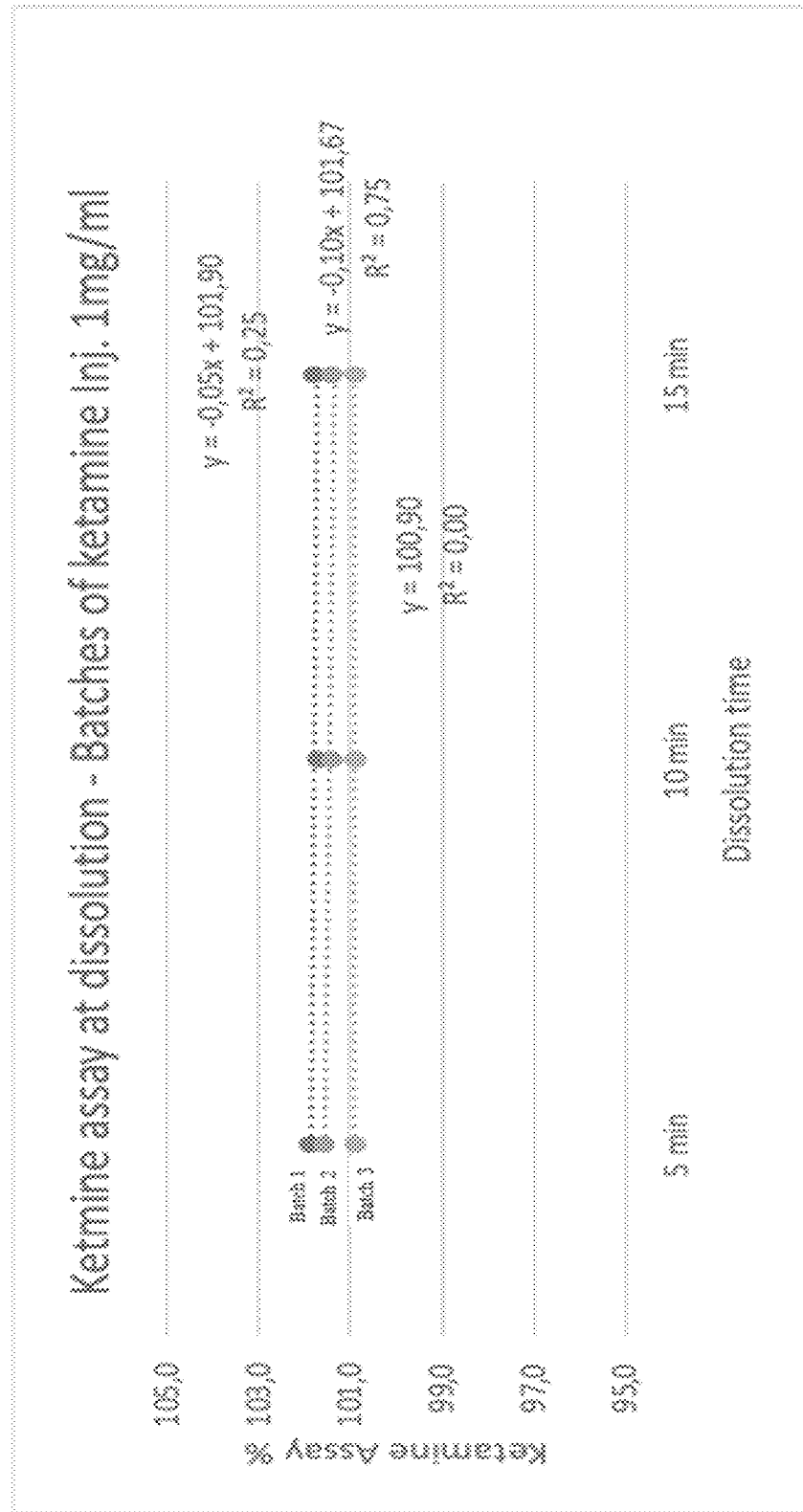
FIG. 5 shows the results of process sampling and analysis of bulk solution for three batches of the ketamine solution of the disclosure at 1 mg/mL.
Figure 6:
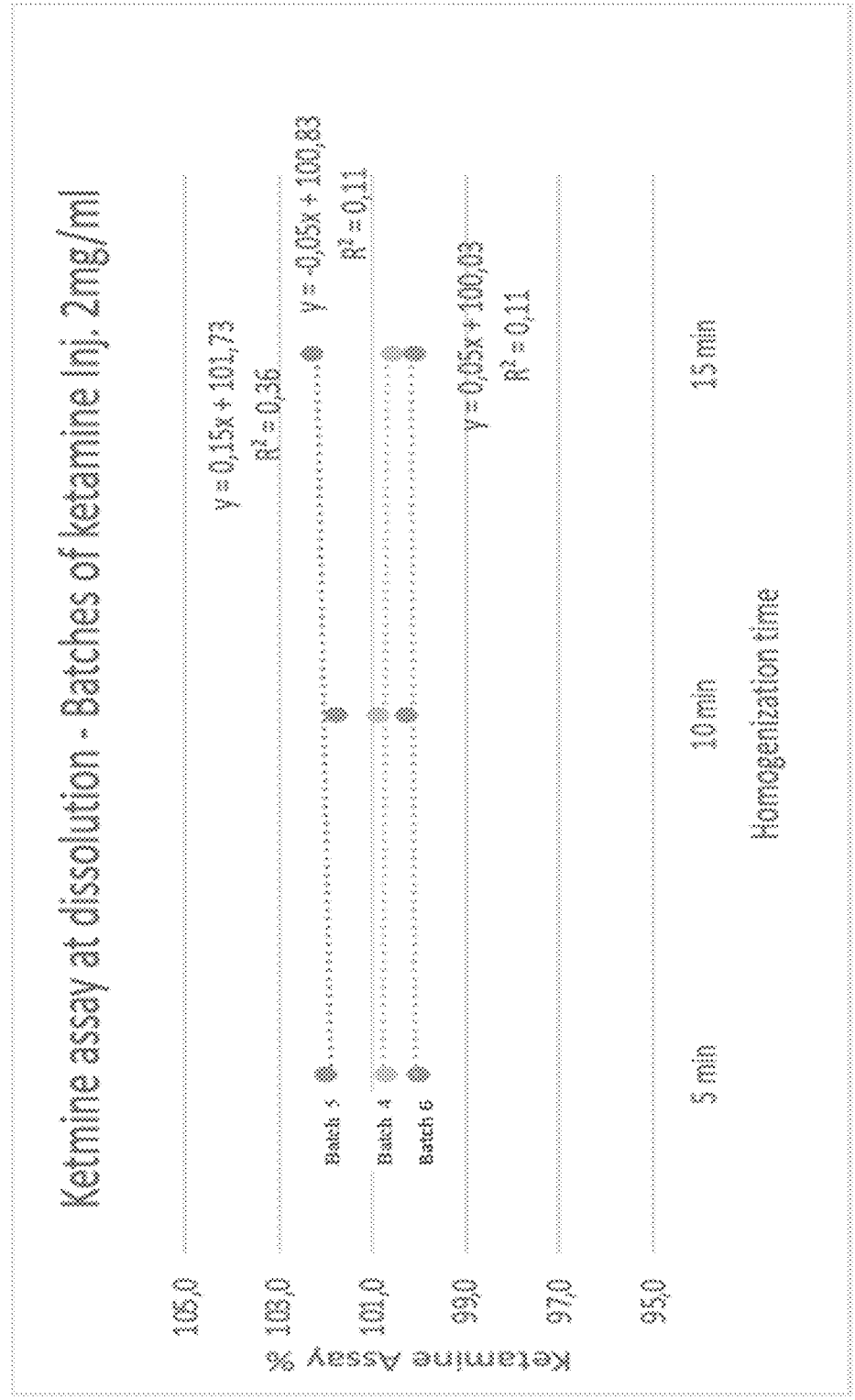
FIG. 6 shows the results of process sampling and analysis of bulk solution for 3 batches of the ketamine solution of the disclosure at 2 mg/mL.

Complete dissolution was verified by in process sampling and analysis of bulk solution before terminal sterilization as shown in FIGS. 5 and 6 and Table 23.

TABLE 23

Test results of Dissolution

| | | | | 1 mg/mL (as in Table 1) | | | 2 mg/mL (as in Table 2) | | |
|---|---|---|---|---|---|---|---|---|---|
| Test | Limits | Units | Dissolution Time | Batch 1 | Batch 2 | Batch 3 | Batch 4 | Batch 5 | Batch 6 |
| Appearance | Clear, colorless to slightly yellowish solution free from visible particles | n/a | 5 min | comply | comply | comply | comply | comply | comply |
| | | | 10 min | comply | comply | comply | comply | comply | comply |
| | | | 15 min | comply | comply | comply | comply | comply | comply |
| pH | * | pH Units | 5 min | 5.0 | 4.8 | 5.3 | 5.1 | 4.8 | 5.2 |
| | | | 10 min | 5.0 | 4.8 | 5.2 | 4.9 | 4.8 | 5.3 |
| | | | 15 min | 5.0 | 4.7 | 5.2 | 5.0 | 4.8 | 5.2 |
| Conductivity | 14.3-15.3 (for information only) | mS/cm | 5 min | 15.3 | 15.3 | 15.3 | 15.1 | 15.1 | 15.0 |
| | | | 10 min | 15.3 | 15.2 | 15.3 | 15.2 | 15.0 | 15.0 |
| | | | 15 min | 15.3 | 15.2 | 15.3 | 14.7 | 15.0 | 14.9 |
| Bulk solution Density | 1.002-1.005 (for information only) | g/mL | 5 min | n/a | n/a | n/a | n/a | n/a | n/a |
| | | | 10 min | n/a | n/a | n/a | n/a | n/a | n/a |
| | | | 15 min | 1.004 | 1.004 | 1.004 | 1.004 | 1.004 | 1.004 |
| Ketamine Assay | 95.0-105.0 | % of Ketamine base | 5 min | 101.9 | 101.6 | 100.9 | 100.7 | 102.0 | 100.0 |
| | | | 10 min | 101.7 | 101.4 | 100.9 | 100.9 | 101.8 | 100.3 |
| | | | 15 min | 101.8 | 101.4 | 100.9 | 100.6 | 102.3 | 100.1 |
| Sodium Chloride Assay | 146.0-162.0 | mmol/L | 5 min | 156.9 | 153.7 | 154.9 | 155.9 | 155.8 | 154.5 |
| | | | 10 min | 157.6 | 155.7 | 155.0 | 156.4 | 156.2 | 154.6 |
| | | | 15 min | 157.2 | 156.3 | 154.6 | 155.5 | 156.1 | 154.7 |
| Osmolality | 270-330 | mOsmol/kg | 5 min | 299 | 299 | 289 | 302 | 304 | 302 |
| | | | 10 min | 301 | 293 | 293 | 302 | 305 | 302 |
| | | | 15 min | 296 | 294 | 297 | 299 | 305 | 302 |

Figure 7:
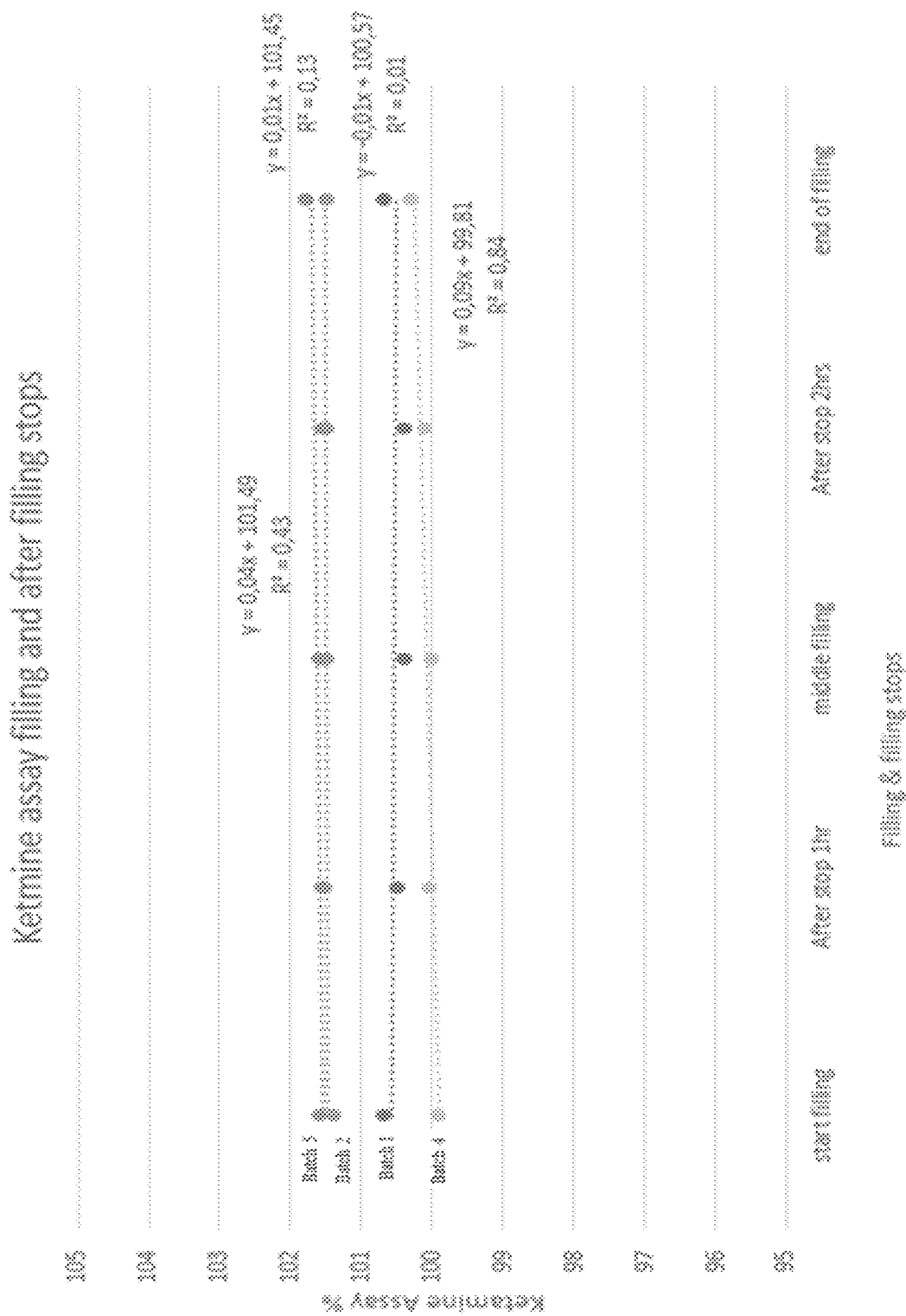
FIG. 7 shows the results of a filter compatibility and filling study for 4 batches of the ready to use sterile infusion bag comprising a preservative-free aqueous ketamine solution at two different concentrations. Batches 1 and 2 are at 1 mg/mL of ketamine and batches 4 and 5 are at 2 mg/mL of ketamine.
Figure 8:
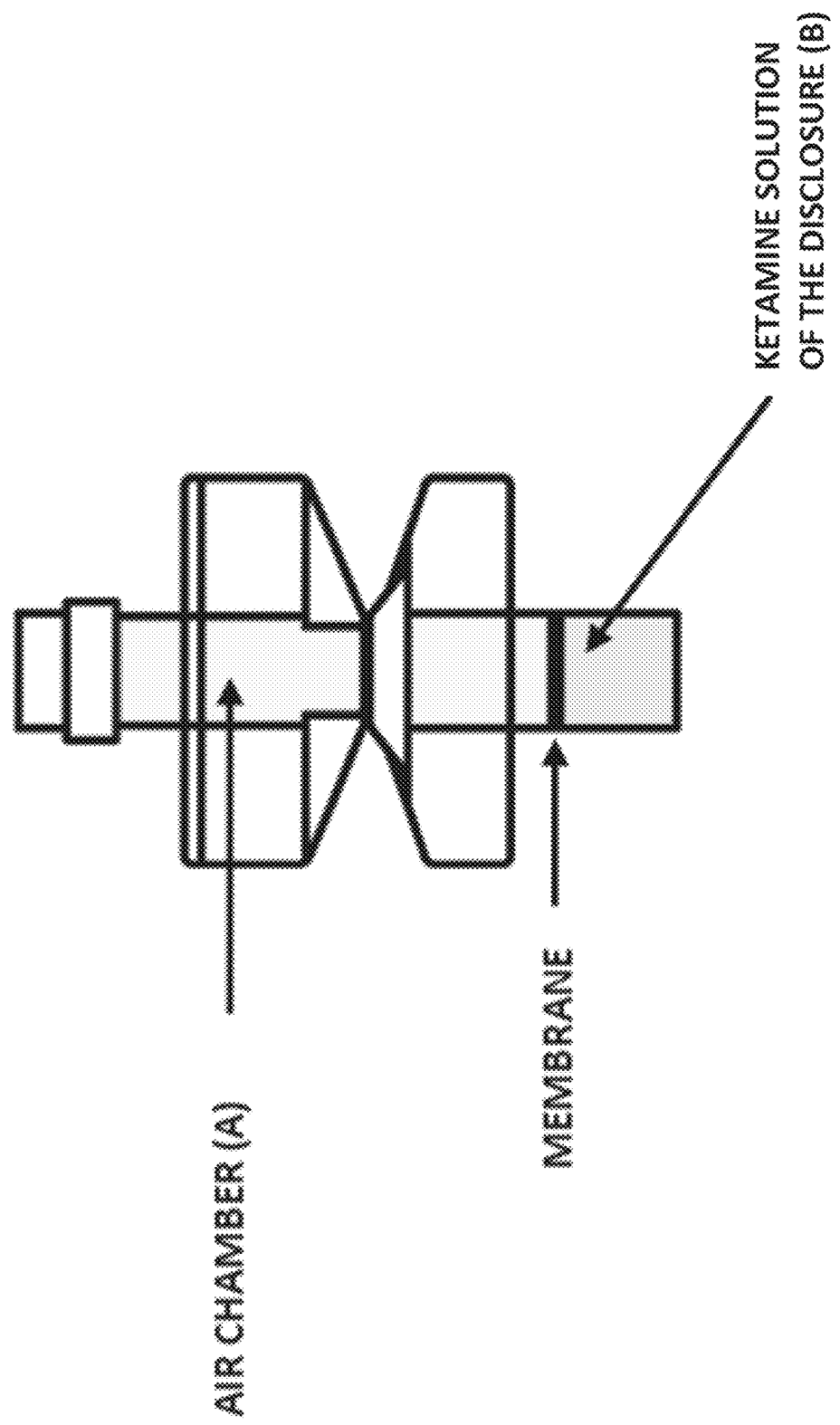
FIG. 8 shows a diagram of a twist off closure that may be used with a sterile infusion bag comprising an aqueous ketamine solution of the disclosure.

The ketamine bulk solution was formulated as in Table 1 (1 mg/ml) and Table 2 (2 mg/ml) then filtered through a pre-filter (3 μm pore size) followed by a filtration through one filter (0.2 μm pore size filters). The in-line filtration was pressure driven (conducted under compressed air) and the drug product was then filled into infusion bags through the tube port in line with filtration. Drug product solution compatibility with the filter and robustness of the filling process was confirmed as shown in FIG. 7.

TABLE 24

Filter Compatibility

| Filling stop duration | Test | Limits | Units | 1 mg/mL Batch 1 | 1 mg/mL Batch 2 | 2 mg/mL Batch 4 | 2 mg/mL Batch 5 |
|---|---|---|---|---|---|---|---|
| 1 Hour | pH (20-25° C.) | 3.5-5.5 | pH Units | 5.3 | 4.7 | 4.9 | 4.8 |
| | | | | 5.3 | 4.7 | 4.9 | 4.8 |
| | | | | 5.3 | 4.7 | 4.9 | 4.8 |
| | Ketamine Assay | 95.0-105.0 | % of ketamine base | 100.7 | 101.5 | 99.9 | 101.3 |
| | | | | 100.6 | 101.6 | 100.0 | 101.7 |
| | | | | 100.2 | 101.6 | 100.2 | 101.6 |
| 2 Hours | pH (20-25° C.) | 3.5-5.5 | pH Units | 5.3 | 4.8 | 4.9 | 4.9 |
| | | | | 5.3 | 4.8 | 4.9 | 4.8 |
| | | | | 5.1 | 4.8 | 4.9 | 4.8 |
| | Ketamine Assay | 95.0-105.0 | % of ketamine base | 100.4 | 101.5 | 100.1 | 101.6 |
| | | | | 100.5 | 101.6 | 100.1 | 101.6 |
| | | | | 100.3 | 101.4 | 100.1 | 101.5 |

After filling the infusion bag with the ketamine solution, the tube port was sealed using a twist-off closure. Terminal sterilization was then conducted using the autoclave process described in Example 2. The closure and tube port are thermally sealed due to the autoclave temperature.

Figure 4:
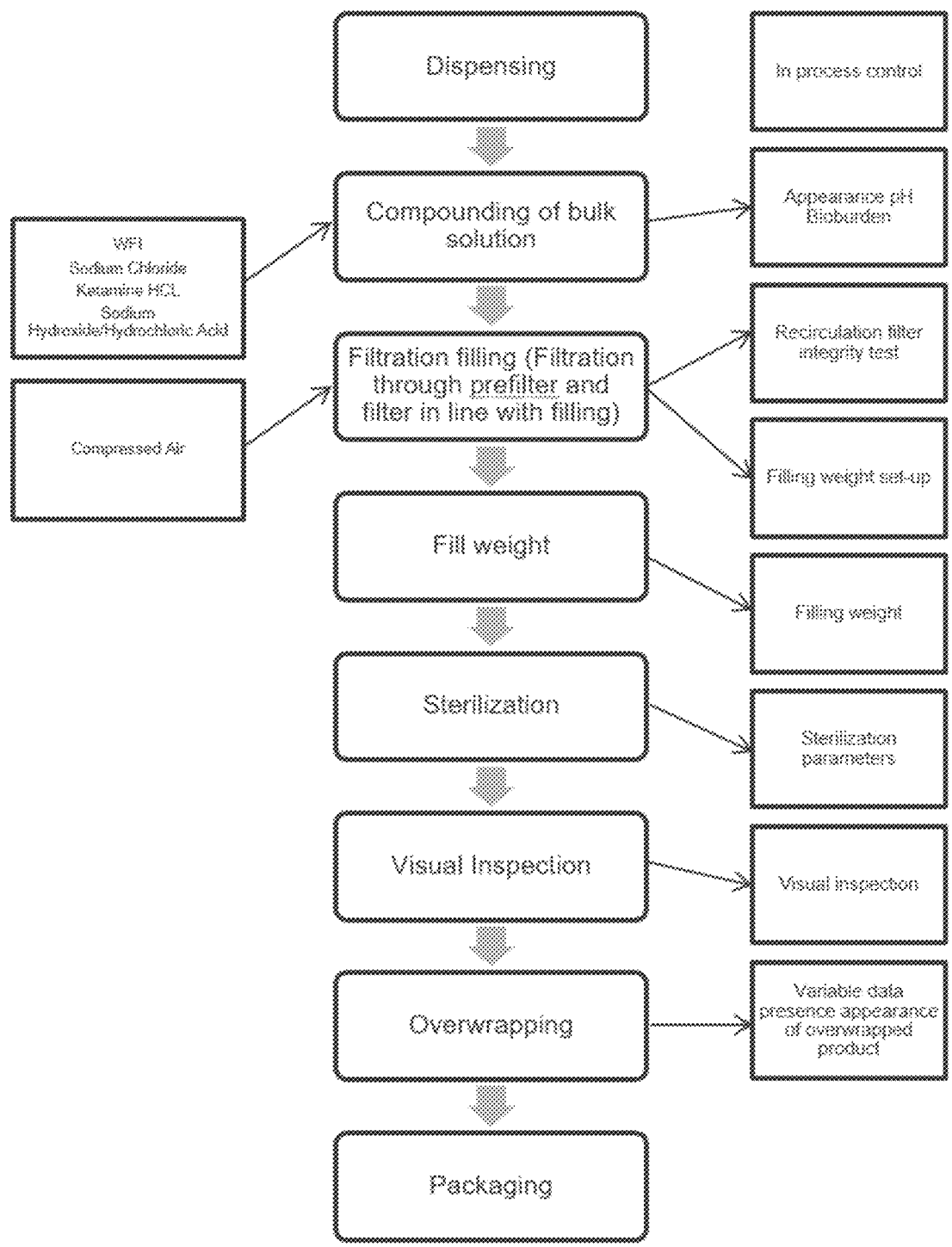
FIG. 4 shows the manufacturing steps for the ready to use terminally sterilized infusion bag comprising a preservative-free aqueous ketamine solution of the disclosure.

These results demonstrate that the manufacturing process in accordance to the procedure shown in FIG. 4 is compatible with manufacturing the ketamine product of the invention as no significant change is noted in the characteristics of the ketamine solution (such as the ketamine assay, pH, etc.) during the dissolution and filtering steps.

It is to be understood that any particular aspect of the present disclosure that falls within the prior art may be excluded from any one or more of the claims. Since such aspects are deemed to be part of the whole of the present disclosure, any part of the whole disclosure may be excluded even if the exclusion is not set forth explicitly herein. Additionally, it is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

The invention claimed is:

1. A ketamine product comprising an aqueous ketamine solution comprising about 0.5 to about 2.5 mg/mL ketamine, a tonicity adjusting agent, and water for injection, wherein the ketamine solution is preservative-free and anti-microbial free, wherein the ketamine product is sterile and ready-to-use (RTU), wherein the pH of the aqueous ketamine solution is about 3.5 to about 5.5, and wherein the ketamine product has a shelf-life of more than six months when stored at a controlled room temperature between 15-30° C.

2. The ketamine product of claim 1, wherein the ketamine product has been terminally sterilized.

3. The ketamine product of claim 1, wherein the ketamine is at a concentration of about 1 mg/mL to about 2 mg/mL.

4. The ketamine product of claim 1, wherein the aqueous ketamine solution is contained in an infusion bag comprising at least one port sealed with a closure.

5. The ketamine product of claim 1, wherein the aqueous ketamine solution has an osmolality of about 270-330 mOsmol/kg.

6. The ketamine product of claim 4, wherein the at least one port comprises a multilayer polyolefin and styrene block copolymer tube material.

7. The ketamine product of claim 4, wherein the closure comprises a plastic material.

8. The ketamine product of claim 4, wherein the closure is a twist-off closure and comprises a membrane that creates a barrier, splitting the twist-off closure in two parts, wherein a first of the two parts is an inferior part of the membrane that is in direct contact with the ketamine solution, and the second of the two parts is a superior part of the membrane that is in contact with a zone that forms an air chamber into the closure.

9. The ketamine product of claim 7, wherein the closure is a twist-off closure that comprises polypropylene (PP), low density polyethylene (LDPE), polyolefin block copolymer, or any combination thereof.

10. The ketamine product of claim 4, wherein the infusion bag comprises a flexible multilayer film comprising a polymer selected from the group consisting of polyethylene, polypropylene, modified polyolefin-polyethylene polymers, styrene-polyolefin based polymers, block copolymers, and a combination thereof.

11. The ketamine product of claim 4, wherein the infusion bag comprises a flexible multilayer film comprising 2 to 5 layers, wherein at least one layer comprises polypropylene styrene-block copolymer.

12. The ketamine product of claim 4, wherein the infusion bag comprises a 3-layer film wherein at least one layer comprises polypropylene styrene-block copolymer.

13. The ketamine product of claim 4, wherein the infusion bag is contained within an overwrap.

14. The ketamine product of claim 13, wherein the overwrap comprises four layers comprising polyester, aluminum, polypropylene, and polyester.

15. The ketamine product of claim 1, wherein the ketamine product has been autoclaved.

16. A ketamine product comprising an aqueous ketamine solution comprising about 0.5 to about 2.5 mg/mL ketamine, a tonicity adjusting agent, and water for injection, wherein the ketamine solution is preservative-free and anti-microbial free, wherein the pH of the aqueous ketamine solution is about 3.5 to about 5.5, and wherein the ketamine solution is contained in a terminally sterilized, ready-to-use infusion container, and wherein the ketamine product has a shelf-life of more than six months when stored at a controlled room temperature between 15-30° C.

17. The ketamine product of claim 16, wherein the tonicity adjustment agent comprises sodium chloride, dextrose, glycerin, mannitol, potassium chloride, or any combination thereof.

18. The ketamine product of claim 1, wherein the ketamine or a pharmaceutically acceptable salt thereof is chemically stable following 24 months of storage at 25° C.±2° C. with relative humidity (RH) at 40%±5%.

19. The ketamine product of claim 1, wherein the ketamine content of the aqueous ketamine solution after accelerated storage at 40° C.±2° C./<25% RH for 6 months is greater than 97%; and/or wherein the ketamine content of the aqueous ketamine solution after long-term storage for 12 months at 25° C.±2° C./40% RH±5% RH is 97% or greater compared to the ketamine content before storage.

20. A method of treating a subject in need of analgesia, comprising administering the ketamine product of claim 1 to the subject as a continuous infusion.

21. A ketamine product comprising an aqueous ketamine solution comprising about 0.5 to about 2.5 mg/mL ketamine, a tonicity adjusting agent, and water for injection, wherein the ketamine solution is preservative-free and anti-microbial free, wherein the pH of the aqueous ketamine solution is about 3.5 to about 5.5, wherein the ketamine solution is contained in an infusion bag, wherein the ketamine product has been aseptically filled, and wherein the ketamine product is sterile and ready-to-use (RTU), and wherein the ketamine product has a shelf-life of more than six months when stored at a controlled room temperature between 15-30° C.

22. The ketamine product of claim 16, wherein the ketamine or a pharmaceutically acceptable salt thereof is chemically stable following 24 months of storage at 25° C.±2° C. with relative humidity (RH) at 40%±5%.

23. The ketamine product of claim 21, wherein the ketamine or a pharmaceutically acceptable salt thereof is chemically stable following 24 months of storage at 25° C.±2° C. with relative humidity (RH) at 40%±5%.

\* \* \* \* \*